US00RE45048E

(19) United States
(12) Reissued Patent
Feng et al.

(10) Patent Number: US RE45,048 E
(45) Date of Reissued Patent: Jul. 22, 2014

(54) METHODS FOR WEED CONTROL USING PLANTS HAVING DICAMBA-DEGRADING ENZYMATIC ACTIVITY

(71) Applicant: Monsanto Technology LLC, St. Louis, MO (US)

(72) Inventors: Paul C. C. Feng, Wildwood, MO (US); Ronald J. Brinker, Ellisville, MO (US)

(73) Assignee: Monsanto Technology LLC, St. Louis, MO (US)

(21) Appl. No.: 13/751,021

(22) Filed: Jan. 25, 2013

Related U.S. Patent Documents

Reissue of:
(64) Patent No.: 7,855,326
Issued: Dec. 21, 2010
Appl. No.: 11/758,653
Filed: Jun. 5, 2007

U.S. Applications:
(60) Provisional application No. 60/811,276, filed on Jun. 6, 2006.

(51) Int. Cl.
*A01H 5/00* (2006.01)
*A01N 37/10* (2006.01)

(52) U.S. Cl.
USPC ..... 800/300; 504/129; 504/144

(58) Field of Classification Search
None
See application file for complete search history.

(56) References Cited

U.S. PATENT DOCUMENTS

| | | | |
|---|---|---|---|
| 4,816,403 | A | 3/1989 | Roy |
| 5,094,945 | A | 3/1992 | Comai |
| 5,188,642 | A | 2/1993 | Shah et al. |
| 5,254,799 | A | 10/1993 | De Greve et al. |
| 5,362,865 | A | 11/1994 | Austin |
| 5,445,962 | A | 8/1995 | Atallah et al. |
| 5,463,175 | A | 10/1995 | Barry et al. |
| 5,491,084 | A | 2/1996 | Chalfie et al. |
| 5,561,236 | A | 10/1996 | Leemans et al. |
| 5,627,061 | A | 5/1997 | Barry et al. |
| 5,633,435 | A | 5/1997 | Barry et al. |
| 5,633,437 | A | 5/1997 | Bernasconi et al. |
| 5,656,422 | A | 8/1997 | Crawford et al. |
| 5,659,122 | A | 8/1997 | Austin |
| 5,670,454 | A | 9/1997 | Grossmann et al. |
| 5,728,925 | A | 3/1998 | Herrera-Estrella et al. |
| 5,850,019 | A | 12/1998 | Maiti et al. |
| 5,939,602 | A | 8/1999 | Volrath et al. |
| 6,040,497 | A | 3/2000 | Spencer et al. |
| 6,146,826 | A | 11/2000 | Chalfie et al. |
| 6,268,549 | B1 | 7/2001 | Sailland et al. |
| 6,376,754 | B1 | 4/2002 | Schillinger et al. |
| 6,414,222 | B1 | 7/2002 | Gengenbach et al. |
| 6,586,367 | B2 | 7/2003 | Lee et al. |
| 6,613,963 | B1 | 9/2003 | Gingera et al. |
| 7,022,896 | B1 | 4/2006 | Weeks et al. |
| RE39,247 | E | 8/2006 | Barry et al. |
| 7,105,724 | B2 | 9/2006 | Weeks et al. |
| 7,230,163 | B2 | 6/2007 | Becton et al. |
| 7,385,106 | B2 | 6/2008 | Stein et al. |
| 7,405,074 | B2 | 7/2008 | Castle et al. |
| 7,405,347 | B2 | 7/2008 | Hammer et al. |
| 7,407,913 | B2 | 8/2008 | Lee et al. |
| 7,429,691 | B2 | 9/2008 | Zhang et al. |
| 7,462,481 | B2 | 12/2008 | Castle et al. |
| 7,622,641 | B2 | 11/2009 | McCutchen et al. |
| 7,812,224 | B2 | 10/2010 | Weeks et al. |
| 7,838,729 | B2 | 11/2010 | Feng et al. |
| 7,851,670 | B2 | 12/2010 | Wan et al. |
| 7,855,326 | B2 | 12/2010 | Feng et al. |
| 7,884,262 | B2 | 2/2011 | Clemente et al. |
| 7,939,721 | B2 | 5/2011 | Arnevik et al. |
| 8,022,272 | B2 | 9/2011 | Heim et al. |
| 8,084,666 | B2 | 12/2011 | Feng et al. |
| 8,119,380 | B2 | 2/2012 | Weeks et al. |
| 8,247,662 | B2 | 8/2012 | Kim |
| 8,420,888 | B2 | 4/2013 | Feng et al. |
| 2001/0046945 | A1 | 11/2001 | Lee et al. |
| 2002/0168680 | A1 | 11/2002 | Barry et al. |
| 2003/0041357 | A1 | 2/2003 | Jepson et al. |
| 2003/0083480 | A1 | 5/2003 | Castle et al. |
| 2003/0115626 | A1 | 6/2003 | Weeks et al. |
| 2003/0135879 | A1 | 7/2003 | Weeks et al. |
| 2004/0082770 | A1 | 4/2004 | Castle et al. |
| 2004/0097373 | A1 | 5/2004 | Lee et al. |
| 2004/0177399 | A1 | 9/2004 | Hammer et al. |
| 2005/0235379 | A1 | 10/2005 | Luo et al. |
| 2006/0019828 | A1 | 1/2006 | Beecher et al. |
| 2006/0111240 | A1 | 5/2006 | Hacker et al. |
| 2006/0218663 | A1 | 9/2006 | Castle et al. |
| 2006/0235215 | A1 | 10/2006 | Cooper |
| 2007/0010398 | A1 | 1/2007 | Rosinger et al. |
| 2007/0079393 | A1 | 4/2007 | McCutchen et al. |
| 2008/0015110 | A1 | 1/2008 | Clemente et al. |
| 2008/0120739 | A1 | 5/2008 | Wan et al. |
| 2008/0305952 | A1 | 12/2008 | Arnevik et al. |
| 2009/0029861 | A1 | 1/2009 | Feng et al. |

(Continued)

FOREIGN PATENT DOCUMENTS

| | | |
|---|---|---|
| CA | 2165036 | 6/1996 |
| CN | 1236394 A | 11/1999 |

(Continued)

OTHER PUBLICATIONS

U.S. Appl. No. 60/811,276, filed Jun. 6, 2006, Feng et al.

(Continued)

*Primary Examiner* — Eileen B O Hara

(74) *Attorney, Agent, or Firm* — Dentons US LLP; Pamela Sisson

(57) ABSTRACT

The invention provides methods for weed control with dicamba and related herbicides. It was found that pre-emergent applications of dicamba at or near planting could be made without significant crop damage or yield loss. The techniques can be combined with the herbicide glyphosate to improve the degree of weed control and permit control of herbicide tolerant weeds.

39 Claims, No Drawings

(56) References Cited

U.S. PATENT DOCUMENTS

| | | | |
|---|---|---|---|
| 2009/0081760 | A1 | 3/2009 | D'Ordine et al. |
| 2009/0093366 | A1 | 4/2009 | Wright et al. |
| 2009/0105077 | A1 | 4/2009 | Bhatti et al. |
| 2010/0279866 | A1 | 11/2010 | Bhatti et al. |
| 2011/0061137 | A1 | 3/2011 | Weeks et al. |
| 2011/0126307 | A1 | 5/2011 | Feng et al. |
| 2011/0152096 | A1 | 6/2011 | Feng et al. |
| 2011/0203017 | A1 | 8/2011 | Wright et al. |
| 2011/0245080 | A1 | 10/2011 | Arnevik et al. |
| 2012/0151620 | A1 | 6/2012 | Feng et al. |
| 2013/0198886 | A1 | 8/2013 | Feng et al. |

FOREIGN PATENT DOCUMENTS

| | | | |
|---|---|---|---|
| CN | 1332800 | A | 1/2002 |
| CN | 1541270 | A | 10/2004 |
| DE | 19919993 | A1 | 11/2000 |
| WO | WO 97/41228 | | 11/1997 |
| WO | WO 98/20144 | | 5/1998 |
| WO | WO 98/39419 | A1 | 9/1998 |
| WO | WO 98/45424 | | 10/1998 |
| WO | WO 00/08936 | | 2/2000 |
| WO | WO 00/08939 | | 2/2000 |
| WO | WO 00/26371 | | 5/2000 |
| WO | WO 00/29596 | | 5/2000 |
| WO | WO 02/26995 | | 4/2002 |
| WO | WO 02/068607 | | 9/2002 |
| WO | WO 2003/006660 | | 1/2003 |
| WO | WO 03/024221 | A1 | 3/2003 |
| WO | WO 03/034813 | | 5/2003 |
| WO | WO 03/096811 | A1 | 11/2003 |
| WO | WO 2004/009761 | | 1/2004 |
| WO | WO 2004/074443 | | 9/2004 |
| WO | WO 2004/101797 | | 11/2004 |
| WO | WO 2005/003362 | | 1/2005 |
| WO | WO 2005/107437 | | 11/2005 |
| WO | WO 2006/065815 | | 6/2006 |
| WO | WO 2007/143690 | | 12/2007 |
| WO | WO 2007/146706 | | 12/2007 |
| WO | WO 2008/048964 | | 4/2008 |
| WO | WO 2008/051633 | | 5/2008 |
| WO | WO 2008/105890 | | 9/2008 |

OTHER PUBLICATIONS

U.S. Appl. No. 60/884,854, filed Jan. 12, 2007, D'Ordine et al.

U.S. Appl. No. 12/875,747, filed Sep. 30, 2010, Weeks et al.

U.S. Appl. No. 12/914,901, filed May 26, 2011, Feng et al.

U.S. Appl. No. 12/942,905, filed Nov. 9, 2010, Feng et al.

U.S. Appl. No. 13/035,902, filed Oct. 26, 2011, Arnevik et al.

Al-Khatib et al., "Foliar absorption and translocation of dicamba from aqueous solution and dicamba-treated soil deposits," *Weed Technology,* 6:57-61, 1992.

Baker, "Response of cotton (*Gossypium hirsutum*) to preplant-applied hormone-type herbicides," *Weed Technology,* 7:150-153, 1993.

"Banvel Herbicide," In: Crop Protection Reference, 11$^{th}$ Edition, pp. 1803-1821, 1995.

"Banvel Herbicide" Product Insert, undated.

Batie et al., "Purification and characterization of phthalate oxygenase and phthalate oxygenase reductase from *Pseudomonas cepacia," J. of Bio. Chem.,* 262(4); 1510-1518, 1987.

Batie et al., "Phthalate dioxygenase reductase and related flavin-iron-sulfur containing electron transferases," In: Chemistry and Biochemistry of Flavoproteins, Muller (Ed.), CRC Press, Boca Raton, FL, pp. 543-556, 1992.

Becker, et al, The cab-m7 gene: a light-inducible, mesophyll-specific gene of maize; *Plant Mol. Bio.* 20: 49-60, 1992.

Behrens et al., "Dicamba resistance: enlarging and preserving biotechnology-based weed management strategies," *Science,* 316:1185-1188, 2007.

Bernhardt et al., "A 4-methoxybenzoate O-demethylase from *Pseudomonas putida.* A new type of monoxygenase system," *Eur. J. Biochem.,* 57(1):241-256, 1975.

Bevan, "Structure and transcription of the nopaline synthase gene region of T-DNA," *Nucleic Acids Res.,* 11(2):369-385, 1983.

Bohlmann, et al, "Purification and cDNA cloning of anthranilate synthase from *Ruta graveolens:* modes of expression and properties of native and recombinant enzymes," *The Plant J.* 7(3): 491-501, Mar. 1993.

Buchanan-Wollaston, et al. Detoxification of the herbicide Dalapon by transformed plants, *J. Cell. Biochem.,* 13D, Abstract No. M503, p. 330, 1989.

Butler et al., "Structure-function analysis of the bacterial aromatic ring-hydroxylating dioxygenases," *Advances in Microbial Physiology,* 38:47-85, 1997.

Carrington et al., "Cap-independent enhancement of translation by a plant potyvirus 5' nontranslated region," *J. of Virology,* 4:1590-1597, Apr. 1990.

Clark, et al., "Nucleotide sequence of a wheat (*Triticum aestivum* L.) cDNA clone encoding the waxy protein," *Plant Mol. Bio.* 16:1099-1101, Jun. 1991.

Comai et al., "Expression in plants of a mutant aroA gene from *Salmonella typhimurium* confers tolerance to glyphosate," *Nature,* 317:741-744, 1985.

Cork et al., "Microbial transformations of herbicides and pesticides," *Adv. Appl. Microbiology,* 36:1-67, 1991.

Cork et al., "Detection, isolation, and stability of megaplasmid-encoded chloroaromatic herbicide-degrading genes within *Pseudomonas* species," *Adv. Appl. Microbiol.,* 40:289-321, 1995.

Coruzzi, et al., "Tissue-specific and light-regulated expression of pea nuclear gene encoding the small subunit of ribulose-1,5-bisphosphate carboxylase," *EMBO J.,* :(8):1671-1679, 1984.

Coruzzi et al., "Nucleotide Sequences of Two Pea cDNA Clones Encoding the Small Subunit of Ribulose 1,5-Bisphosphate Carboxylase and the Major Chlorophyll a/b-binding Thylakoid Polypeptide," *J. of Biological Chem.* 258(3): 1399-1402, Feb. 1983.

Creissen et al., "Molecular characterization of glutathione reductase cDNAs from pea (*Pisum sativum* L.)," *Plant J.*, 2(1):129-131, 1992.

Creissen et al., "Simultaneous targeting of pea glutathione reductase and of a bacterial fusion protein to chloroplasts and mitochondria in transgenic tobacco," *Plant J.,* 8:167-175, 1995.

De Block et al., "Engineering herbicide resistance in plants by expression of a detoxifying enzyme," *EMBO J.*, 6(9):2513-2518, 1987.

Dehmel et al., "Cloning, nucleotide sequence and expression of the gene encoding a novel dioxygenase involved in metabolism of carboxydiphenyl ethers in *Pseudomonas pseudoalcaligenes* POB310," *Arch. Microbiol.,* 163:35-41, 1995.

Depicker et al., "Nopaline synthase: transcript mapping and DNA sequence," *J. Mol. Appl. Genet.,* 1:561-573, 1982.

Dernoeden et al., "Fenoxaprop Activity Influenced by Auxin-like Herbicide Application Timing," Department of Agronomy, University of Maryland, *HortScience* 29(12):1518-1519, 1994.

Desvaux et al., "Genomic analysis of the protein secretion systems in *Clostridium acetobutylicum* ATCC 824," *Biochimica et Biophysica Acta,* 1745:223-253, 2005.

Eckes et al., "Isolation and characterization of a light-inducible, organ-specific gene from potato and analysis of its expression after tagging and transfer into tobacco and potato shoots," *Mol. Gen. Genet.,* 205:14-22, 1986.

Fogarty et al., "Microbiological degradation of the herbicide dicamba," *J. of Industrial Microbiology,* 14:365-370, 1995.

Fukumori et al., "Purification and characterization of 2,-dichlorophenoxyacetate/α-ketoglutarate dioxygenase," *J. Biol. Chem.,* 268:24311-24317, 1993.

Gardiner et al., "Anchoring 9,371 maize expressed sequence tagged unigenes to the bacterial artificial chromosome contig map by two-dimensional overgo hybridization," *Plant Physiol.,* 134:1317-1326, 2004.

Gasser et al., "Structure, expression, and evolution of the 5-enolpyruvylshikimate-3-phosphate synthase genes of petunia and tomato," *J. Biol. Chem.,* 263:4280-4287, 1988.

GenBank Accession No. V00087, Mar. 18, 1996.

(56) References Cited

OTHER PUBLICATIONS

GenBank Accession No. AY786443, dated Jun. 29, 2005.
GenBank Accession No. E01312, Nov. 4, 2005.
GenBank Accession No. AAT48249, 2004.
Gibson et al., "Aromatic hydrocarbon dioxygenases in environmental biotechnology," *Current Opinion in Biotechnology,* 11:236-243, 2000.
Gurbiel, et al., "Active site structure of Rieske-type proteins: electron nuclear double resonance studies of isotopically labeled phthalate dioxygenase from *Pseudomonas cepacia* and Rieske protein from *Rhodobacter capsulatus* and molecular modeling studies of a Rieske center," *Biochemistry,* 35(24):7834-7845, 1996 (Abstract).
Hajdukiewicz et al., "The small, versatile pPZP family of *Agrobacterium* binary vectors for plant transformation," *Plant Mol. Biol.,* 25:989-994, 1994.
Hamill et al., "Weed control in glufosinate-resistant corn (*Zea mays*)", *Weed Technology* 14(3):578-585, 2000.
Herman et al., "A three-component dicamba O-demethylase from *Pseudomonas maltophilia,* Strain Di-6," *J. of Biological Chemistry,* 280(26):24759-24767, 2005.
Hoffman et al., "Type I hyperlipoproteinemia due to a novel loss of function mutation of lipoprotein lipase, Cys(239)→Trp, associated with recurrent severe pancreatitis," *J. Clin. Endocrinol. Metab.,* 85(12):4795-4798, 2000.
Jordan et al., "Italian Ryegrass Control with Preplant Herbicides," *The J of Cotton Science,* 5:268-274; 2001.
Khalil et al., "Plasmid-mediated catabolism of dicamba by *Pseudomonsas* species strain PXM," *Microbios,* 102:183-191, 2000.
Klee et al., "Cloning of an *Arabidopsis thaliana* gene encoding 5-enolpyruvylshikimate-3-phosphate synthase: sequence analysis and manipulation to obtain glyphosate-tolerant plants," *Mol. Gen. Genet.,* 210:437-442, 1987.
Koncz et al., "The promoter of $T_L$-DNA gene 5 controls the tissue-specific expression of chimaeric genes carried by a novel type of *Agrobacterium* binary vector," *Mol. Gen. Genet.,* 204:383-396, 1986.
Krueger et al., "Isolation and identification of microorganisms for the degradation of dicamba," *J. Agric. Food Chem.,* 37:534-538, 1989.
Krueger et al., "Use of dicamba-degrading microorganisms to protect dicamba susceptible plant species," *J. of Agri. and Food Chem.,* 39(5):1000-1003, 1991.
Magnusson et al., "Tolerance of soybean (*Glycine max*) and sunflower (*Helianthus annuus*) to fall-applied dicamba," *Weed Sci.,* 35:846-852, 1987.
Markus et al., "Purification and some properties of component A of the 4-chlorophenylacetate 3,4-dioxygenase from *Pseudomonas* species strain CBS," *J. of Biol. Chem.,* 261(27):12883-12888, 1986.
Mason et al., "The electron-transport proteins of hydroxylating bacterial dioxygenases," *Ann. Rev. of Microbiology,* 46:277-305, 1992.
Mazur et al., "Sequence of a genomic DNA clone for the small subunit of ribulose bis-phosphate carboxylase-oxygenase from tobacco," *Nucleic Acids Res.,* 13(7):2373-2386, 1985.
Misawa et al., "Functional expression of the *Erwinia uredovora* carotenoid biosynthesis gene crt1 in transgenic plants showing an increase of beta-carotene biosynthesis activity and resistance to the bleaching herbicide norflurazon," *Plant J.,* 4:833-840, 1993.
Misawa et al., "Expression of an *Erwinia* phytoene desaturase gene not only confers multiple resistance to herbicides interfering with carotenoid biosynthesis but also alters xanthophyll metabolism in transgenic plants," *Plant J.,* 6:481-489, 1994.
Mitsuhara et al., "Efficient promoter cassettes for enhanced expression of foreign genes in dicotyledonous and monocotyledonous plants," *Plant Cell Physiol.,* 37:49-59, 1996.
Morgan et al. "Chemical cotton stalk destruction: what will be the herbicide options in the future," presentation given at the 57th Annual Beltwide Cotton Production Conference, Wednesday, Jan. 4, 2012.
Mueller et al., "Proactive Versus Reactive Management of Glyphosate-Resistant or - Tolerant Weeds", *Weed Technology* 19:924-933, 2005.
Okagaki, "Nucleotide sequence of a long cDNA from the rice waxy gene," *Plant Mol. Biol.,* 19:513-516, 1992.
Padgette et al., "Development, identification and characterization of a glyphosate-tolerant soybean line," *Crop Sci.,* 35:1451-1461, 1995.
Peniuk et al., "Physiological investigations into the resistance of a wild mustard (*Sinapis arvensis* L.) biotype to auxinic herbicides," *Weed Research,* 33:431-440, 1993.
Sarpe et al., "Researches on resistance of maize hybrids and inbred lines to the herbicides based on 2,4-D and dicamba," *Fragmenta Herbologica Jugoslavica,* 16(1-2):299-305, 1987.
Sathasivan et al., "Nucleotide sequence of a mutant acetolactate synthase gene from an imidazolinone-resistant *Arabidopsis thaliana* var. Columbia," *Nucl. Acids. Res.,* 18(8):2188, 1990.
Schroeder et al., "Soft red winter wheat (*Triticum aestivum*) response to dicamba and dicamba plus 2,4-D," *Weed Technology,* 3:67-71, 1989.
Spencer et al., "Segregation of transgenes in maize," *Plant Molecular Biology,* 18:201-210, 1992.
Sprague, "Avoid herbicide spray tank contamination," *IPM News,* ipmnews.msu.edu/fieldcrop/tabid/56, Mar. 24, 2010.
Stalker et al., "Herbicide resistance in transgenic plants expressing a bacterial detoxification gene," *Science,* 242:419-423, 1988.
Streber et al., "Transgenic tobacco plants expressing a bacterial detoxifying enzyme are resistant to 2,4-D," *Bio/Technology,* 7:811-816, 1989.
Svab et al., "Aminoglycoside-3"-adenyltransferase confers resistance to spectinomycin and streptomycin in *Nicotiana tabacum," Plant Mol. Biol.,* 14:197, 1990.
Svab et al., "Stable transformation of plastids in higher plants," *Proc. Natl. Acad. Sci. USA,* 87(21):8526-8530, 1990.
Third Party Submission in a Published Application Under 37 C.F.R. § 1.99 dated Dec. 2, 2011.
Thompson et al., "Soybean tolerance to early preplant applications of 2,4-D ester, 2,4-D amine, and dicamba," *Weed Technology,* 21:882-885, 2007.
Tredaway-Ducar et al., "Site-specific weed management in corn (*Zea mays*)", *Weed Technology* 17(4):711-717, 2003.
Wada et al., "Molecular characterization of coagulation factor XII deficiency in a Japanese family," *Thromb. Haemost.,* 90(1):59-63, 2003.
Wang, "Characterization of cellular and enzymatic degradation of dicamba by *Pseudomonas maltophilia,* Strain DI-6," Thesis, University of Nebraska, Aug. 1996.
Wang et al., "A three-component enzyme system catalyzes the O demethylation of the herbicide dicamba in *Pseudomonas maltophilia* DI-6," *Applied and Environmental Microbiology,* 63(4):1623-1626, 1997.
Weeks et al., "Characterization of a bacterial system capable of degrading dicamba and evaluation of its potential in the development of herbicide-tolerant crops," *J. of Cellular Biochemistry,* Supplement 18A:91, 1994.
Xiaoman et al., "Study of BRCA1 gene in hereditary breast and ovarian cancer," *Chin. Med. Sci. J.,* 14(4):195-199, 1999.
Zuver et al., "Evaluation of postemergence weed control strategies in herbicide-resistant isolines of corn (*Zea mays*)", *Weed Technology* 20(1):172-178, 2006.
Office Action regarding U.S. Appl. No. 10/330,662 dated Apr. 18, 2006.
Interview Summary regarding U.S. Appl. No. 10/330,662, dated Sep. 13, 2006.
Terminal Disclaimer filed in U.S. Appl. No. 10/330,662, dated Oct. 18, 2006.
Declaration of Donald P. Weeks regarding U.S. Appl. No. 10/330,662, dated Oct. 18, 2006.
Amendment and Response to Office Action regarding U.S. Appl. No. 10/330,662, dated Oct. 18, 2006.
Final Office Action regarding U.S. Appl. No. 10/330,662, dated Jan. 10, 2007.
Amendment and Response to Office Action regarding U.S. Appl. No. 10/330,662, dated Jul. 9, 2007.
Amendment regarding U.S. Appl. No. 10/330,662, dated Jul. 20, 2007.
Office Action regarding U.S. Appl. No. 10/330,662, dated Sep. 21, 2007.

(56) References Cited

OTHER PUBLICATIONS

Declaration of Donald P. Weeks regarding U.S. Appl. No. 10/330,662, dated Feb. 20, 2008.
Amendment and Response to Office Action regarding U.S. Appl. No. 10/330,662, dated Mar. 20, 2008.
Office Action regarding U.S. Appl. No. 10/330,662, dated Jul. 9, 2008.
Amendment and Remarks regarding U.S. Appl. No. 10/330,662, dated Jan. 9, 2009.
Final Office Action regarding U.S. Appl. No. 10/330,662, dated Apr. 24, 2009.
Office Action regarding U.S. Appl. No. 11/758,657 dated Sep. 2, 2009.
Office Action regarding U.S. Appl. No. 11/758,656, dated Sep. 15, 2009.
Amendment and Remarks regarding U.S. Appl. No. 10/330,662, dated Sep. 24, 2009.
Office Action regarding U.S. Appl. No. 11/758,659 dated Nov. 24, 2009.
Response to Office Action regarding U.S. Appl. No. 11/758,656, dated Dec. 17, 2009.
Response to Office Action regarding U.S. Appl. No. 11/758,657, dated Jan. 4, 2010.
Office Action regarding U.S. Appl. No. 10/330,662, dated Jan. 11, 2010.
Interview Summary regarding U.S. Appl. No. 10/330,662, dated Mar. 19, 2010.
Final Office Action regarding U.S. Appl. No. 11/758,656, dated Apr. 14, 2010.
Final Office Action regarding U.S. Appl. No. 11/758,657, dated Apr. 14, 2010.
Office Action regarding U.S. Appl. No. 11/758,660, dated Apr. 28, 2010.
Amendment and Remarks regarding U.S. Appl. No. 10/330,662, dated May 4, 2010.
Amendment and Response to Office Action regarding U.S. Appl. No. 11/758,659, dated May 24, 2010.
Notice of Allowance regarding U.S. Appl. No. 10/330,662, dated Jul. 12, 2010.
Response to Final Office Action regarding U.S. Appl. No. 11/758,657, dated Jul. 14, 2010.
Notice of Allowance regarding U.S. Appl. No. 11/758,659, dated Aug. 3, 2010.
Declaration of Yuechun Wan Under 37 C.F.R. §1.132, dated Aug. 11, 2010.
Amendment and Response to Final Office Action regarding U.S. Appl. No. 11/758,656, dated Aug. 13, 2010.
Notice of Allowance regarding U.S. Appl. No. 11/758,657, dated Sep. 10, 2010.
Response to Office Action regarding U.S. Appl. No. 11/758,660, dated Sep. 27, 2010.
Office Action regarding Honduran Patent Application No. 2009-00795, dated Sep. 27, 2010.
Notice of Allowance regarding U.S. Appl. No. 11/758,656, dated Oct. 4, 2010.
Office Action regarding Honduran Patent Application No. 2009-00795, dated Dec. 22, 2010.
English translation of Office Action regarding Honduran Patent Application No. 2009-00795, dated Dec. 22, 2010.
Response to Final Office Action regarding U.S. Appl. No. 11/758,660, filed Jan. 13, 2011.
Terminal Disclaimer filed in U.S. Appl. No. 11/758,660, filed Jan. 13, 2011.
Notice of Allowance regarding U.S. Appl. No. 11/758,660, dated Jan. 28, 2011.
Office Action regarding U.S. Appl. No. 12/914,901 dated Apr. 26, 2011.
Response to Office Action regarding U.S. Appl. No. 12/914,901 dated Jun. 8, 2011.
Office Action regarding U.S. Appl. No. 12/942,905, dated Jul. 7, 2011.
Notice of Allowance regarding U.S. Appl. No. 12/914,901 dated Aug. 25, 2011.
Response to Office Action regarding U.S. Appl. No. 12/942,905, dated Aug. 30, 2011.
Terminal Disclaimer for U.S. Appl. No. 12/942,905, dated Aug. 30, 2011.
Notice of Non-Compliant Amendment regarding U.S. Appl. No. 12/942,905, dated Sep. 14, 2011.
Response to Non-Compliant Amendment regarding U.S. Appl. No. 12/942,905, dated Sep. 28, 2011.
Petition for Determination of Nonregulated Status for Dicamba-Tolerant Soybean MON 87707, pp. 1, 2 and 77; Oct. 10, 2011.
Notice of Allowance for U.S. Appl. No. 12/942,905, dated Oct. 24, 2011.
Office Action regarding U.S. Appl. No. 13/035,902 dated Dec. 15, 2011.
Request for Continued Examination for U.S. Appl. No. 12/942,905, dated Jan. 24, 2012.
Response to Office Action regarding U.S. Appl. No. 13/035,902 dated Feb. 7, 2012.
Final Office action regarding U.S. Appl. No. 13/035,902 dated Apr. 2, 2012.
EPO, Partial Search Report for Application No. 12155307.7-2403, Apr. 12, 2012.
Request for Continued Examination and Amendment filed in U.S. Appl. No. 13/035,902, filed Jul. 2, 2012.
USPTO: Non-final Office Action for U.S. Appl. No. 13/326,204, dated Sep. 17, 2012.
Response and Amendment to Non-final Office Action for U.S. Appl. No. 13/326,204, dated Nov. 6, 2012.
USPTO; Office Action in U.S. Appl. No. 13/774,794 dated Oct. 4, 2013.
Response to Office Action regarding U.S. Appl. No. 13/774,794, filed Dec. 19, 2013.
USPTO: Notice of Allowance regarding U.S. Appl. No. 13/855,631, issued on Feb. 10, 2014.
USPTO; Notice of Allowance in U.S. Appl. No. 12/942,905 dated Sep. 17, 2013.
USPTO; Notice of Allowance in U.S. Appl. No. 13/326,204 dated Dec. 10, 2012.
USPTO; Office Action in U.S. Appl. No. 11/758,660 dated Dec. 2, 2010.
European Search Report issued in Application No. 12181146.7 dated Nov. 14, 2012.
USPTO: Notice of Allowance regarding U.S. Appl. No. 13/774,794, issued on Mar. 21, 2014.
Amendment and Response to Final Office Action regarding U.S. Appl. No. 11/758,656, dated Aug. 16, 2010.
U.S. Appl. No. 12/440,173, filed Mar. 5, 2009, Bhatti et al.
U.S. Appl. No. 12/875,747, filed Sep. 3, 2010, Weeks et al.

METHODS FOR WEED CONTROL USING PLANTS HAVING DICAMBA-DEGRADING ENZYMATIC ACTIVITY

Matter enclosed in heavy brackets [ ] appears in the original patent but forms no part of this reissue specification; matter printed in italics indicates the additions made by reissue.

This application claims the priority of U.S. Provisional Patent Application 60/811,276, filed Jun. 6, 2006, the disclosure of which is incorporated herein by reference in its entirety.

BACKGROUND OF THE INVENTION

1. Field of the Invention

The invention relates generally to the field of weed management. More specifically, the invention relates to methods for using auxin-like herbicides such as dicamba for controlling weeds.

2. Description of the Related Art

Weeds cost farmers billions of dollars annually in crop losses and the expense of efforts to keep weeds under control. Weeds also serve as hosts for crop diseases and insect pests. The losses caused by weeds in agricultural production environments include decreases in crop yield, reduced crop quality, increased irrigation costs, increased harvesting costs, decreased land value, injury to livestock, and crop damage from insects and diseases harbored by the weeds. The principal means by which weeds cause these effects are: 1) competing with crop plants for the essentials of growth and development, 2) production of toxic or irritant chemicals that cause human or animal health problem, 3) production of immense quantities of seed or vegetative reproductive parts or both that contaminate agricultural products and perpetuate the species in agricultural lands, and 4) production on agricultural and nonagricultural lands of vast amounts of vegetation that must be disposed of. The damage caused can be significant. For example, it is estimated that between 1972 and 1976 corn yields were reduced by about 10% due to weeds (Chandler, 1981).

Among weeds that serve as hosts for crop pests, for example, pepperweed and tansymustard (Descurainia sp.) maintain large populations of diamondback moths during the late fall, winter, and spring. They are also hosts to the turnip aphid and green peach aphid. Several weed species of the nightshade family (Solanaceae) are hosts to insects that commonly attack eggplant, pepper, potato, and tomato. For example, horsenettle (Solanum carolinense L.) is a host of the Colorado potato beetle, and black nightshade (S. nigrum L.) is a host of the cabbage looper. Morning-glory is an important host of insects attacking sweet potato, especially the highly destructive sweet potato weevil. Ragweed serves as a host for Mansonia mosquitoes, an insect vector for the human diseases encephalitis and rural filariasis.

Some weeds are undesirable in hay, pastures, and rangelands because of the mechanical injury that they inflict on livestock. Woody stems, thorns, and stiff seed awns cause injury to the mouth and digestive tract of livestock; and the hairs and fibers of some plants tend to ball up and obstruct the intestines, especially in horses, causing serious problems. Ingested by milk cows, some weeds such as ragweeds, wild garlic (Allium vineale L.), and mustard, among others, impart a distinctly distasteful odor or flavor to milk and butter.

Barbed seed dispersal units may become so entangled in the wool of sheep as to greatly diminish its market value. Parasitic plants, such as dodder (Cuscuta sp.), broomrape (Orobanche sp.), and witchweed, rob their host plants of organic foodstuffs.

Chemical herbicides have provided an effective method of weed control over the years. Herbicides can generally be applied pre-emergence and/or post-emergence. Pre-emergence herbicides are applied in a field before a crop emerges from the soil. Such applications are typically applied to the soil before, at the same time, or soon after planting the crop. Such applications may kill weeds that are growing in the field prior to the emergence of the crop, and may also prevent or reduce germination of weeds that are present in the soil. Post-emergence herbicides are typically used to kill weeds after a crop has emerged in the field. Such applications may kill weeds in the field and prevent or reduce future weed germination. In either case, the herbicides may be applied to the surface of the soil, mixed with the soil, over the top of the plant, or applied by any other method known to those of skill in the art.

One weed control strategy is to apply an herbicide such as dicamba to a field before sowing seeds. However, after applying the herbicide to a field, a farmer has to wait at least several weeks before sowing the field with crop seeds such that the herbicide has killed most of the weeds and has degraded so as not injure the sown crop. For example, plants are especially sensitive to dicamba and it has been recommended that dicamba formulations such as Banvel™ or Sterling™ be applied 30 days prior to planting for controlling weeds. A comprehensive list of weeds that are controlled by dicamba is available (Anonymous, 2007). The herbicide is particularly useful for control of taller weeds and more difficult to control weeds such as purslane, sicklepod, morninglory and wild buckwheat. Dicamba can be used to control weeds not susceptible to other herbicides. Following the application of Clarity™, another formulation of dicamba, a minimum accumulation of one inch of rainfall or overhead irrigation followed by a 14 day waiting period for the 4 to 8 ounce/acre rates or a 28 day waiting period for the 16 ounce/acre rates has been recommend for controlling weeds in a soybean field (see Table 22 in VanGessel and Majek, 2005). Also, the Clarity® label recommends that it be applied at least 15 days prior to sorghum planting. Similarly, for cotton, a waiting period of 21 days is recommended after applying Clarity® or Banvel® to the field, before planting the cotton seeds (Craig et al., 2005, Crop Profile for Cotton (Gossypium hirsutum) in Tennessee, www.ipmcenters.org/cropprofiles/docs/tncotton.html) and no pre-emergence and post-emergence application are recommended. The waiting period is also dependent on the crop growing environment at any give time, such as the type of soil (soil having organic activity will degrade dicamba faster), moisture content, rainfall, temperature, as well as type of formulation and rate of application.

The herbicide 2,4-D has been recommended for controlling certain weeds in a soybean field such as mustard spp., plantains, marestail, and 2,4-D susceptible annual broadleaf weeds by applying it 7 to 30 days prior to planting, depending on rate and formulation (ester or amine) (see Table 22 in VanGessel and Majek, 2005).

One method that has been successfully used to manage weeds combines herbicide treatments with crops that are tolerant to the herbicides. In this manner, herbicides that would normally injure a crop can be applied before and during growth of the crop without causing damage. Thus, weeds may be effectively controlled and new weed control options are made available to the grower. In recent years, crops tolerant to several herbicides have been developed. For example, crops tolerant to 2,4-dichlorophenoxyacetic acid (Streber and Willmitzer, 1989), bromoxynil (Stalker et al., 1988), glyphosate (Comai et al., 1985) and phosphinothricin (De Block et al., 1987) have been developed.

Recently, a gene for dicamba monooxygenase (DMO) was isolated from Pseudomonas maltophilia (US Patent Application No: 20030135879) which is involved in the conversion of a herbicidal form of the herbicide dicamba (3,6-dichloro-o-anisic acid) to a non-toxic 3,6-dichlorosalicylic acid. The inventors reported the transformation of the DMO gene into tobacco and Arabidopsis. The transformed plant tissue was selected on kanamycin and regenerated into a plant. However, herbicide tolerance was not demonstrated or suggested in immature tissues or seedlings or in other plants. Pre-emergence herbicide tolerance to dicamba was not described. Transgenic soybean plants and other plants tolerant to application of dicamba are described in Behrens et al. (2007).

Dicamba is one member of a class of herbicides commonly referred to as "auxin-like" herbicides or "synthetic auxins." These herbicides mimic or act like the natural plant growth regulators called auxins. Auxin-like herbicides appear to affect cell wall plasticity and nucleic acid metabolism, which can lead to uncontrolled cell division and growth. The injury symptoms caused by auxin-like herbicides include epinastic bending and twisting of stems and petioles, leaf cupping and curling, and abnormal leaf shape and venation.

Dicamba is one of the many auxin-like herbicides that is a low-cost, environmentally-friendly herbicide that has been used as a pre-emergence herbicide (i.e., 30 days prior to planting) in dicots and as a pre- and/or post-emergence herbicide in corn, sorghum, small grains, pasture, hay, rangeland, sugarcane, asparagus, turf, and grass seed crops to effectively control annual and perennial broadleaf weeds and several grassy weeds (Crop Protection Chemicals Reference, 1995). Unfortunately, dicamba can injure many commercial crops including beans, soybeans, cotton, peas, potatoes, sunflowers, tomatoes, tobacco, and fruit trees, ornamental plants and trees, and other broadleaf plants when it comes into contact with them. Soybean and cotton are particularly sensitive to dicamba. Thus, applications of dicamba must generally occur several weeks before planting of sensitive crops to ensure that residual dicamba is sufficiently cleared from the crop environment before crops emerge. For post-emergent weed control in corn, dicamba is the 5th most widely used herbicide for broad leaf weeds. However, although the optimal rate for broad leaf weed control is between 280 to 560 g/h (grams/hectare), the average use rate in corn is 168 g/h as at higher use rates and under certain environmental conditions, dicamba can injure corn.

As noted above, current manufacturer's guidelines typically require at least a 30 day delay between the application of dicamba and the planting of sensitive crops. This inability to apply dicamba close to the time that crops are planted delays sowing time and shortens the growing season, thereby increasing the risk of exposing crops to frost in the fall. The delay also means that the farmers have to go through the field twice; once for planting and once for spraying, thereby increasing fuel and wear-tear costs to the farmers. Improvements over the state of the art that would eliminate the delay would positively impact the quality and quantity of the crop which could result and reduce economic losses to farmers. More effective weed control would also reduce the risk of weeds developing resistance to existing herbicides.

SUMMARY OF THE INVENTION

In one aspect, the invention provides a method for controlling weed growth in a field comprising: a) applying a herbicidally effective amount of an auxin-like herbicide to a crop-growing environment; and planting a transgenic seed of a dicotyledonous plant expressing a nucleic acid encoding dicamba monooxygenase in soil of the crop-growing environment, wherein the seed germinates within 30 days or less of applying the herbicide and wherein the dicamba monooxygenase comprises at least 70% sequence identity to the polypeptide sequence of SEQ ID NO:2; and c) allowing the seed to germinate into a plant. In certain embodiments, the seed germinates within four weeks, three weeks, two weeks, or less than one week after treating the growing environment with the auxin-like herbicide. The treated growing environment may be, for example, a field in which a crop is planted. A population of seeds of a plant tolerant to the auxin-like herbicide may be planted in the field. Treating the environment can be carried out according to known techniques in the art using, for example, commercially available formulations of auxin-like herbicides such as dicamba. The environment includes an area for which control of weeds is desired and in which the seed of a plant tolerant to the auxin-like herbicide can be planted. A weed can be directly contacted with herbicide in the environment and soil in the environment can be contacted with the herbicide, preventing or reducing weed growth in the soil. The step of treating the environment with a herbicide may be carried out before, after, or concurrently with the step of planting the soil with the transgenic seed. The transgenic seed may be planted into soil in the environment, for example, within three weeks before or after treatment, including from between about two weeks, one week and 0 weeks before or after treatment, further including from between about 1, 2, 3, 4, 5, or 6 days before or after treatment, including concurrently with treatment. In the method, the seed may germinate, for example, from between about 30 days and 0 days after treating the environment, including between about 21, 18, 16, 14, 12, 10, 8, 6, 5, 4, 3, 2, 1 and about 0 days after treating the environment. The method may further comprise applying one or more additional treatments of an auxin-like herbicide after the seed germinates and/or the plant is growing. In certain embodiments, a second treatment is carried out at a time selected from the group consisting of between about the 1 to 2 leaf and 3 to 4 leaf stages, before flowering, at flowering, after flowering, and at seed formation. In one embodiment, the second treatment comprises applying dicamba and/or a 2,4-dichlorophenoxyacetic compound (2,4-D).

In a method of the invention, the auxin-like herbicide may be selected from the group consisting of a phenoxy carboxylic acid compound, benzoic acid compound, pyridine carboxylic acid compound, quinoline carboxylic acid compound, and benazolinethyl compound. Examples of a phenoxy carboxylic acid compound include 2,4-dichlorophenoxyacetic acid and (4-chloro-2-methylphenoxy)acetic acid. In certain embodiments, a herbicidally effective amount of 2,4-D and/or (4-chloro-2-methylphenoxy)acetic acid used is between about 2 g/ha (grams/hectare) to about 5000 g/ha, including about 50 g/ha to about 2500 g/ha, about 60 g/ha to about 2000 g/ha, about 100 g/ha to about 2000 g/ha, about 75 g/ha to about 1000 g/ha, about 100 g/ha to about 500 g/ha, and from about 100 g/ha to about 280 g/ha. In one embodiment found to function particularly well with the invention, dicamba is used as the herbicide. In certain embodiments, a herbicidally effective amount of dicamba used may be from about 2.5 g/ha to about 10,080 g/ha, including about 2.5 g/ha to about 5,040 g/ha, about 5 g/ha to about 2,020 g/ha, about 10 g/a to about 820 g/h and about 50 g/ha to about 1,000 g/ha, about 100 g/ha to about 800 g/ha and about 250 g/ha to about 800 g/ha.

In a method of the invention a plant may be used exhibiting tolerance to auxin-like herbicides including dicamba. Such a plant may comprise a nucleic acid encoding a dicamba monooxygenase. In one embodiment, the plant is defined as comprising a nucleic acid encoding a dicamba monooxygenase that has at least 70% identity to a polypeptide sequence of any one or more of SEQ ID NOs:2, 4, 6, 8, 10 or 12, including at least about 75%, 80%, 85%, 90%, 95%, 97%, 98%, 99% and greater sequence identity to these sequences. Polypeptide or polynucleotide comparisons may be carried out and identity determined as is known in the art, for example, using MEGAlign (DNAStar, Inc., 1228 S. Park St., Madison, Wis. 53715) with default parameters. Such software matches similar sequences by assigning degrees of similarity or identity.

The methods of the invention may be used in connection with plants that exhibit susceptibility to auxin-like herbicides such as dicotyledonous (dicot) plants. In certain embodiments, a dicotyledonous plant is used selected from the group consisting of alfalfa, beans, broccoli, cabbage, carrot, cauliflower, celery, cotton, cucumber, eggplant, lettuce, melon, pea, pepper, pumpkin, radish, rapeseed, spinach, soybean, squash, tomato, and watermelon. In some embodiments, the dicot is soybean, cotton, or canola.

In another aspect, the invention provides a method for controlling a weed in a field comprising: a) planting a transgenic seed in a field, wherein the seed comprises transgenes conferring tolerance to an auxin-like herbicide and a second herbicide; b) growing the seed into a plant; and c) treating the field with an amount of the auxin-like herbicide and the second herbicide in amounts effective to control weed growth. In some embodiments, the second herbicide may be glufosinate (De Block et al., 1987), a sulfonylurea (Sathasiivan et al., 1990), an imidazolinone (U.S. Pat. Nos. 5,633,437; 6,613,963), bromoxynil (Stalker et al., 1988), dalapon or 2,2-Dichloropropionic acid (Buchanan-Wollaston et al., 1989), cyclohexanedione (U.S. Pat. No. 6,414,222), a protoporphyrinogen oxidase inhibitor (U.S. Pat. No. 5,939,602), norflurazon (Misawa et al., 1993 and Misawa et al., 1994), or isoxaflutole (WO 96/38567) herbicide, among others. The auxin-like herbicide and the second herbicide may be applied simultaneously or separately. In a particular embodiment, the second herbicide is glyphosate and the auxin-like herbicide is dicamba. In one embodiment, the plant comprises a nucleic acid that has at least 70% sequence identity to a nucleic acid sequence of any one or more of SEQ ID NOs: 1, 3, 5, 7, 9, or 11, including at least about 75%, 80%, 85%, 90%, 95%, 97%, 98%, 99% and greater sequence identity to these sequence.

In further embodiments, a plant such as the foregoing is defined as comprising a transgene conferring glyphosate tolerance. Glyphosate resistant 5-enolpyruvylshikimate-3-phosphate synthases (EPSPS) are well known in the art and disclosed, for example, in U.S. Pat. Nos. 5,627,061, 5,633,435, 6,040,497, 5,094,945, WO04074443, and WO04009761. Nucleic acids encoding glyphosate degrading enzymes, for example, glyphosate oxidoreductase (GOX, U.S. Pat. No. 5,463,175), and nucleic acids encoding glyphosate inactivating enzymes, such as glyphosate-N-acetyl transferase (GAT, U.S. Patent publication 20030083480; U.S. Patent Publication 20070079393) and glyphosate decarboxylase (WO05003362 and U.S. Patent Application No. 20040177399) are also known. In certain embodiments, the GAT enzyme comprises the sequence of GAT4601 (SEQ ID NO:19), or is encoded by a transgene comprising the nucleic acid sequence of SEQ ID NO:18. In a particular embodiment, the GAT polypeptide is expressed using the SCP1 promoter.

In the method, treating the field may be carried out at a time selected from the group consisting of between about the 1 to 2 leaf and 3 to 4 leaf stages, before flowering, at flowering, after flowering, and at seed formation. Treating the field may further be defined as carried out at a time proximate to step a) such that the seed germinates while the auxin-like herbicide remains in the soil in an amount effective to control growth of the weed. In the method, treating the field may be carried out about three weeks, two weeks 1 week or 0 weeks before step a). The auxin-like herbicide may be selected from the group consisting of a phenoxy carboxylic acid compound, benzoic acid compound, pyridine carboxylic acid compound, quinoline carboxylic acid compound, and benazolinethyl compound.

The phenoxy carboxylic acid compound may be selected from the group consisting of 2,4-dichlorophenoxyacetic acid, (4-chloro-2-methylphenoxy)acetic acid, and 4-(2,4-dichlorophenoxy)butyric acid (2,4-DB). The amount of 2,4-dichlorophenoxyacetic compound used may be lower than about 280 g/ha. The amount of 4-(2,4-dichlorophenoxy)butyric acid (2,4-DB) used may be lower than about 1120 g/ha. The amount of (4-chloro-2-methylphenoxy) acetic acid compound used may be lower than about 280 g/ha. In one embodiment, the auxin like herbicide is dicamba. The amount of dicamba used may be, for example, from about 2.5 g/ha to about 10,080 g/ha, including about 2.5 g/ha to about 1040 g/ha, about 5 g/ha to about 2040 g/ha, about 10 g/a to about 820 g/h, and about 50 g/ha to about 1000 g/ha. The amount of glyphosate may be from about 200 g/ha to about 1,600 g/h, including from about 200 g/ha to about 1,000 g/h, from about 200 g/ha to about 800 g/h, from about 200 g/ha to about 400 g/h, and from about 400 g/ha to about 800 g/h.

In yet another aspect, the invention provides a method for controlling weed growth in a crop-growing environment comprising: a) applying a herbicidally effective amount of an auxin-like herbicide to a crop-growing environment; b) planting a transgenic seed of a monocotyledonous plant comprising a nucleic acid encoding a dicamba degrading enzymatic activity, such as dicamba monooxygenase, in soil of the crop-growing environment within 21 days of applying the auxin-like herbicide, wherein the herbicidally effective amount is an amount that does not damage the transgenic seed or a plant that germinates therefrom but will damage a seed or a plant that germinates therefrom of the same genotype that lacks the nucleic acid and is planted under the same conditions as the transgenic seed, wherein the nucleic acid is selected from the group consisting of (1) a nucleic acid sequence encoding the polypeptide of SEQ ID NO:8, (2) a nucleic acid sequence comprising the sequence of SEQ ID NO:7, (3) a nucleic acid sequence that hybridizes to a complement of the nucleic acid sequence of SEQ ID NO:7 under conditions of 5×SSC, 50% formamide and 42° C., (4) a nucleic acid sequence having at least 70% sequence identity to the nucleic acid sequence of SEQ ID NO:7, and (5) a nucleic acid sequence encoding a polypeptide having at least 70% sequence identity to the polypeptide sequence of SEQ ID NO:8; and c) allowing the seed to germinate into a plant. The nucleic acid sequence having at least 70% sequence identity to the nucleic acid sequence of SEQ ID NO:7 may encode a polypeptide comprising a cysteine residue at position 112. This embodiment may combined with any of the methods and compositions provided above.

In particular embodiments of the invention, herbicide treatments to monocot plants may be made at higher rates and/or in closer proximity to emergence of crops than previously could be made without damaging crops. In specific embodiments, a herbicidally effective amount of 2,4-D and/or MCPA, such as, for example, at least about 200, 300, 300, 500, 590, 650, 700, 800 or more g/ha of either or both herbicides, including from about 300 to about 1200 g/ha, from about 500 to about 1200 g/ha, from about 600 to about 1200 g/ha, from about 590 to about 1400 g/ha, and from about 700 to about 1100 g/ha of either or both herbicides. The herbicide may also be dicamba and the herbicidally effective amount may be, for example, at least about 168, 175, 190, 200, 225, 250, 280, 300, 400, 500, 560 or more g/ha of dicamba, including from about 200 g/ha to about 600 g/ha, from about 250 g/ha to about 600 g/ha, from about 250 g/ha to about 800 g/ha, from about 225 g/ha to about 1120 g/ha, and from about 250 g/ha to about 1200 g/ha, from about 280 g/ha to about 1120 g/ha and from about 560 g/ha to about 1120 g/ha. In particular embodiment, the monocotyledonous plant is selected from the group consisting of corn, rice, sorghum, wheat, rye, millet, sugarcane, oat, triticale, switchgrass, and turfgrass. Expressing the transgenic dicamba-degrading enzymatic activity such as a monooxygenase, in a monocotyledonous crop plant, such as corn, allows application of a higher level of dicamba to the crop for the purpose of weed control at any stage of plant growth, as compared to the level of dicamba that may be applied to a monocotyledonous crop plant that does not comprise a transgene that encodes such a dicamba-degrading enzymatic activity.

In yet another aspect, the invention provides a method for controlling weed growth in a field comprising: a) applying a herbicidally effective amount of an auxin-like herbicide other than dicamba to a field, wherein the field comprises a transgenic dicotyledonous plant comprising a nucleic acid encoding dicamba monooxygenase or is planted with a seed that germinates into said transgenic dicotyledonous plant within 21 days of applying the herbicide, wherein the herbicidally effective amount is an amount that does not damage the transgenic dicotyledonous plant but will damage a plant of the same genotype that lacks the nucleic acid encoding dicamba monooxygenase, wherein the nucleic acid is selected from the group consisting of (1) a nucleic acid sequence encoding the polypeptide of SEQ ID NO:8, (2) a nucleic acid sequence comprising the sequence of SEQ ID NO:7, (3) a nucleic acid sequence that hybridizes to a complement of the nucleic acid sequence of SEQ ID NO:7 under conditions of 5×SSC, 50% formamide and 42° C., (4) a nucleic acid sequence having at least 70% sequence identity to the nucleic acid sequence of SEQ ID NO:7, and (5) a nucleic acid sequence encoding a polypeptide having at least 70% sequence identity to the polypeptide sequence of SEQ ID NO:8; and b) allowing the transgenic dicotyledonous plant to grow. In the method, step a) may comprise applying the herbicidally effective amount of an auxin-like herbicide to a growing environment adjacent to a growing environment comprising the transgenic dicotyledonous plant and allowing the herbicide to drift onto the plant or soil in which the plant grows. The auxin-like herbicide may be any herbicide as described herein. In the method, step b) may comprise allowing the transgenic dicotyledonous plant to grow to maturity. In specific embodiments, the herbicidally effective amount may be defined as an amount that does not damage the transgenic plant.

In yet another aspect, the invention provides a method for increasing the efficiency of use of a herbicide delivery device comprising: a) obtaining a device that has been used to deliver a first composition comprising an auxin-like herbicide; and b) delivering a second composition to the field using the device without first completely washing the device so that a herbicide residue comprising the auxin-like herbicide remains in the device and is delivered with the second composition to the field, wherein the field comprises a transgenic dicotyledonous plant expressing a nucleic acid encoding dicamba monooxygenase or is planted with a seed that germinates into said transgenic dicotyledonous plant within 21 days of delivering the second composition, wherein the herbicide residue is present in an amount that does not damage the transgenic dicotyledonous plant but will damage a plant of the same genotype that lacks the nucleic acid encoding dicamba monooxygenase, wherein the nucleic acid is selected from the group consisting of (1) a nucleic acid sequence encoding the polypeptide of SEQ ID NO:8, (2) a nucleic acid sequence comprising the sequence of SEQ ID NO:7, (3) a nucleic acid sequence that hybridizes to a complement of the nucleic acid sequence of SEQ ID NO:7 under conditions of 5×SSC, 50% formamide and 42° C., (4) a nucleic acid sequence having at least 70% sequence identity to the nucleic acid sequence of SEQ ID NO:7, and (5) a nucleic acid sequence encoding a polypeptide having at least 70% sequence identity to the polypeptide sequence of SEQ ID NO:8.

DETAILED DESCRIPTION OF THE INVENTION

The invention relates, in one aspect, to the unexpected discovery that pre-emergent applications of auxin-like herbicides such as dicamba may be made close to, or even concurrently with the planting of crops. The invention provides superior weed control options, including reduction and/or prevention of herbicide tolerance in weeds. Pre-emergent applications of auxin-like herbicides such as dicamba have previously required herbicide applications well in advance of planting and germination of plants susceptible to auxin-like herbicides to allow breakdown of the herbicide in the environment and avoid significant crop damage or death. Most crop plants, and particularly dicotyledonous plants such as soybeans and cotton are extremely sensitive to dicamba. Thus, the recommended post-application delays in planting by manufacturers must be closely followed.

Young plantlets and seeds are particularly sensitive to herbicides. Even in transgenic seeds and plants, immature tissues can insufficiently express the gene needed to render them tolerant to the herbicide, or may not have accumulated sufficient levels of the protein to confer tolerance. For example, mature plants have been found exhibiting high levels of tolerance to the herbicides Harness™ (acetochlor), Lasso™ (alachlor), Treflan™ (Trifluralin), Eptam™ (EPTC), and/or Far-Go™ (triallate) but susceptibility to the herbicides at germination. As a result of this variability in young tissues, crop response to post-emergence applications (e.g., in more mature vegetative tissues) of dicamba herbicides can significantly differ from the crop response to pre-emergent applications of herbicides in which younger more sensitive tissues are exposed. The former does not necessarily predict the latter. This is underscored in the case of plants highly sensitive to a given herbicide, such as dicots and the herbicide dicamba. Thus, the present invention unexpectedly shows that higher than predicted levels of crop safety can be achieved from pre-emergence applications of dicamba.

The present invention employs auxin-like herbicides, which are also called auxinic or growth regulator herbicides, or Group 4 herbicides (based on their mode of action). These types of herbicides mimic or act like the natural plant growth regulators called auxins. The action of auxinic herbicides appears to affect cell wall plasticity and nucleic acid metabolism, which can lead to uncontrolled cell division and growth.

Auxin-like herbicides include four chemical families: phenoxy, carboxylic acid (or pyridine), benzoic acid, and quinaline carboxylic acid. Phenoxy herbicides are most common and have been used as herbicides since the 1940s when (2,4-dichlorophenoxy)acetic acid (2,4-D) was discovered. Other examples include 4-(2,4-dichlorophenoxy)butyric acid (2,4-DB), 2-(2,4-dichlorophenoxy)propanoic acid (2,4-DP), (2,4,5-trichlorophenoxy)acetic acid (2,4,5-T), 2-(2,4,5-Trichlorophenoxy)Propionic Acid (2,4,5-TP), 2-(2,4-dichloro-3-methylphenoxy)-N-phenylpropanamide (clomeprop), (4-chloro-2-methylphenoxy)acetic acid (MCPA), 4-(4-chloro-o-tolyloxy)butyric acid (MCPB), and 2-(4-chloro-2-methylphenoxy)propanoic acid (MCPP).

The next largest chemical family is the carboxylic acid herbicides, also called pyridine herbicides. Examples include 3,6-dichloro-2-pyridinecarboxylic acid (Clopyralid), 4-amino-3,5,6-trichloro-2-pyridinecarboxylic acid (picloram), (2,4,5-trichlorophenoxy) acetic acid (triclopyr), and 4-amino-3,5-dichloro-6-fluoro-2-pyridyloxyacetic acid (fluoroxypyr). Examples of benzoic acids include 3,6-dichloro-o-anisic acid (dicamba) and 3-amino-2,5-dichlorobenzoic acid (choramben). Dicamba is a particularly useful herbicide for use in the present invention. A fourth chemical family of auxinic herbicides is the quinaline carboxylic acid family. Example includes 3,7-dichloro-8-quinolinecarboxylic acid (quinclorac). This herbicide is unique in that it also will control some grass weeds, unlike the other auxin-like herbicides which essentially control only broadleaf or dicotyledonous plants. The other herbicide in this category is 7-chloro-3-methyl-8-quinolinecarboxylic acid (quinmerac).

It was found, for example, that soybean plants transformed with dicamba monooxygenase (DMO)-encoding polynucleotide constructs were tolerant to even early pre-emergence application of dicamba, with less than 10% injury rates at even 9× the labeled application rate (5,040 g/ha, 4.5 lb/acre; Table 1). The inventors found that, even using an 18× application rate of 10,080 g/ha (9 lb/acre), injury to transgenic dicamba tolerant plants was less than 20% (Table 4). At an approximately 2× rate of application of 1122 g/ha, less than 2% injury was observed. It was therefore indicated the improved weed control associated with pre- and post-emergence applications of herbicides may be used without any significant decreases in productivity due to herbicide damage. Pre-emergent applications of dicamba according to the invention may therefore be combined with one or more herbicide applications post-emergence to dicamba-tolerant plants, while maintaining crop yield and obtaining improved weed control. For example, one such herbicide application regime involved a late pre-emergence application of dicamba in conjunction with a post-emergence application of dicamba at the V2 stage of development. In certain embodiments, the post-emergence application may be carried out at any point from emergence to harvest. Particularly beneficial will be post-emergence application at any V stage until the soybean canopy closes, for example, at about the V1, V2, V3, V4, V5, V6 and/or later stages.

In accordance with the invention, methods and compositions for the control of weeds are provided comprising the use of plants exhibiting tolerance to glyphosate and auxin-like herbicides such as dicamba. As shown in the working examples, dicamba and glyphosate allow use of decreased amounts of herbicide to achieve the same level of control of glyphosate-tolerant weeds and thus this embodiment provides a significant advance for the control of herbicide tolerance in commercial production fields. In one embodiment, a tank mix of glyphosate and dicamba is applied pre- and/or post-emergence to plants. Glyphosate and dicamba may additionally be applied separately. In order to obtain the ability to use decreased amount of herbicide, the glyphosate and dicamba are preferably applied within a sufficient interval that both herbicides remain active and able to control weed growth.

This embodiment therefore allows use of lower amounts of either herbicide to achieve the same degree of weed control as an application of only one of the herbicides. For example, the invention provides methods of weed control comprising applying in a field planted with transgenic plants having tolerance to dicamba and glyphosate a herbicide composition comprising less than a 1× rate of glyphosate and/or dicamba, relative to the standard manufacturer labeled rate. Examples of respective glyphosate and dicamba application rates include from about a 0.5×-0.95× of either herbicide, specifically including about 0.5×, 0.6×, 0.7×, 0.8×, 0.85×, 0.9×, and 0.95× of either herbicide and all derivable combinations thereof, as well as higher rates such as 0.97× and 0.99×. Alternatively, in the case of more difficult to control weeds or where a greater degree of weed control is desired, 1× and higher application rates may be made in view of the finding herein that even high application rates of dicamba did not significantly damage plants. The 1× application rates are set by the manufacturer of a commercially available herbicide formulation and are known to those of skill in the art. For example, the label for Fallow Master™, a glyphosate and dicamba mixture having a ratio of glyphosate:dicamba of about 2:1 recommends application rates of about 451 g/ha (311 ae g/ha glyphosate:140 ae g/ha dicamba) to 621 ae g/ha (428 ae g/ha glyphosate: 193 ae g/ha dicamba) depending upon the weed species and weed height.

"Glyphosate" refers to N-phosphonomethylglycine and salts thereof. Glyphosate is commercially available in numerous formulations. Examples of these formulations of glyphosate include, without limitation, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt, ROUNDUP® WEATHERMAX containing glyphosate as its potassium salt; ROUNDUP® DRY and RIVAL® herbicides, which contain glyphosate as its ammonium salt; ROUNDUP® GEOFORCE, which contains glyphosate as its sodium salt; and TOUCHDOWN® herbicide, which contains glyphosate as its trimethylsulfonium salt. "Dicamba" refers to 3,6-dichloro-o-anisic acid or 3,6-dichloro-2-methoxy benzoic acid and its acids and salts. Its salts include isopropylamine, diglycoamine, dimethylamine, potassium and sodium. Examples of commercial formulations of dicamba include, without limitation, Banvel™ (as DMA salt), Clarity™ (as DGA salt), VEL-58-CS-11™ and Vanquish™ (as DGA salt, BASF).

Non-limiting examples of weeds that can be effectively controlled using dicamba are the following: cheese weed, chick weed, while clover, cocklebur, Asiatic dayflower, deadnettle, red stem filaree, Carolina geranium, hemp sesbania, henbit, field horsetail (marestail), knotweed, kochia, lambsquarter, morninglory, indian mustard, wild mustard, redroot pigweed, smooth pigweed, prickly sida, cutleaf evening primrose, common purslane, common ragweed, gaint ragweed, russian thistle, shepardspurse, pennsylvania smartweed, spurge, velvetleaf, field violet, wild buckwheat, wild radish, soybeanpurslane, sicklepod, morninglory, wild buckwheat, common ragweed, horseweed (marestail), hairy fleabane, buckhorn plantain, and palmer pigweed. Non-limiting examples of weeds that can be controlled using dicamba and glyphosate are the following: barnyardgrass, downy brome, volunteer cereals, Persian darnel, field sandbur, green foxtail, wild oats, wild buckwheat, volunteer canola, cowcockle, flixweed, kochia, ladysthumb, lambsquarters, wild mustard, prickly lettuce, redroot pigweed, smartweed, stinkgrass, stinkweed, russian thistle, foxtail, and witchgrass. Combining glyphosate and dicamba achieves the same level of weed control with reduced herbicide amounts and thus the spectrum of weeds that may be controlled at any given herbicide application rate may be increased when the herbicides are combined.

Transgenic plants having herbicide tolerance may be made as described in the art. Dicamba tolerance may be conferred, for example, by a gene for dicamba monooxygenase (DMO) from Pseudomonas maltophilia (US Patent Application No: 20030135879). Examples of sequences that may be used in this regard are nucleic acid encoding the polypeptides of SEQ ID Nos: 2, 4, 6, 8, 10, and 12. Examples of sequences encoding these polypeptides are given as SEQ ID NOS: 1, 3, 5, 7, 9, and 11. SEQ ID NO: 1 shows DMO from Pseudomonas maltophilia optimized for expression in dicots using Arabidopsis thaliana codon usage. The polypeptide, predicted to have an Ala, Thr, Cys at positions 2, 3, 112, respectively, is given in SEQ ID NO:2. SEQ ID NO:3 shows another Pseudomonas maltophilia DMO optimized for expression in dicots and encoding the polypeptide of SEQ ID NO:4, predicted to have an Leu, Thr, Cys at positions 2, 3, 112, respectively. SEQ ID NO:5 shows the coding sequence and SEQ ID NO:6 the polypeptide for dicot optimized DMO predicted to have a Leu, Thr, Trp at positions 2, 3, 112, respectively. SEQ ID NOS:7 and 8 show the coding and polypeptide sequences for DMO predicted to have an Ala, Thr, Cys at position 2, 3, 112, respectively. SEQ ID NOS:9 and 10 show the dicot-optimized coding sequence and polypeptide sequences for DMO predicted to have an Ala, Thr, Trp at positions 2, 3, 112, respectively. SEQ ID NOS:11 and 12 show coding sequence and polypeptide sequences for DMO from Pseudomonas maltophilia (US Patent Application No: 20030135879). Another exemplary DMO sequence may be a DMO predicted to have a Leu, Thr, Cys at position 2, 3, 112, respectively with codon usage of Pseudomonas maltophilia (US Patent Application No: 20030135879).

Sequences conferring glyphosate tolerance are also known, including glyphosate resistant 5-enolpyruvylshikimate-3-phosphate synthases (EPSPS) as described in U.S. Pat. Nos. 5,627,061, 5,633,435, 6,040,497, 5,094,945, WO04074443, WO04009761, all of which are hereby incorporated by reference; by expression of nucleic acids encoding glyphosate degrading enzymes, for example, glyphosate oxidoreductase (GOX, U.S. Pat. No. 5,463,175, herein incorporated by reference), glyphosate decarboxylase (WO05003362; US Patent Application 20040177399, herein incorporated by reference); and by expression of nucleic acids encoding glyphosate inactivating enzymes, such as glyphosate-N-acetyl transferase (GAT, e.g. U.S. Patent publications 20030083480 and 20070079393, herein incorporated by reference).

Variants of proteins having a capability to degrade auxin-like herbicides, glyphosate or other herbicides can readily be prepared and assayed for activity according to standard methods. Such sequences can also be identified by techniques know in the art, for example, from suitable organisms including bacteria that degrade auxin-like herbicides such as dicamba or other herbicides (U.S. Pat. No. 5,445,962; Cork and Krueger, 1991; Cork and Khalil, 1995). One means of isolating a DMO or other sequence is by nucleic acid hybridization, for example, to a library constructed from the source organism, or by RT-PCR using mRNA from the source organism and primers based on the disclosed desaturases. The invention therefore encompasses use of nucleic acids hybridizing under stringent conditions to a DMO encoding sequence described herein. One of skill in the art understands that conditions may be rendered less stringent by increasing salt concentration and decreasing temperature. Thus, hybridization conditions can be readily manipulated, and thus will generally be a method of choice depending on the desired results. An example of high stringency conditions is 5×SSC, 50% formamide and 42° C. By conducting a wash under such conditions, for example, for 10 minutes, those sequences not hybridizing to a particular target sequence under these conditions can be removed.

Variants can also be chemically synthesized, for example, using the known DMO polynucleotide sequences according to techniques well known in the art. For instance, DNA sequences may be synthesized by phosphoamidite chemistry in an automated DNA synthesizer. Chemical synthesis has a number of advantages. In particular, chemical synthesis is desirable because codons preferred by the host in which the DNA sequence will be expressed may be used to optimize expression. Not all of the codons need to be altered to obtain improved expression, but preferably at least the codons rarely used in the host are changed to host-preferred codons. High levels of expression can be obtained by changing greater than about 50%, most preferably at least about 80%, of the codons to host-preferred codons. The codon preferences of many host cells are known (PCT WO 97/31115; PCT WO 97/11086; EP 646643; EP 553494; and U.S. Patent Nos: 5,689,052; 5,567,862; 5,567,600; 5,552,299 and 5,017,692). The codon preferences of other host cells can be deduced by methods known in the art. Also, using chemical synthesis, the sequence of the DNA molecule or its encoded protein can be readily changed to, for example, optimize expression (for example, eliminate mRNA secondary structures that interfere with transcription or translation), add unique restriction sites at convenient points, and delete protease cleavage sites.

Modification and changes may be made to the polypeptide sequence of a protein such as the DMO sequences provided herein while retaining enzymatic activity. The following is a discussion based upon changing the amino acids of a protein to create an equivalent, or even an improved, modified polypeptide and corresponding coding sequences. It is known, for example, that certain amino acids may be substituted for other amino acids in a protein structure without appreciable loss of interactive binding capacity with structures such as binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the DMO peptide sequences described herein or other herbicide tolerance polypeptides and corresponding DNA coding sequences without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte et al., 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those which are within ±1 are particularly preferred, and those within ±0.5 are even more particularly preferred. Exemplary substitutions which take these and various of the foregoing characteristics into consideration are well known to those of skill in the art and include: arginine and lysine; glutamate and aspartate; serine and threonine; glutamine and asparagine; and valine, leucine and isoleucine.

A gene conferring herbicide tolerance will typically be linked to a plant promoter driving expression of the gene in an amount sufficient to confer the herbicide tolerance. Promoters suitable for this and other uses are well known in the art. Examples describing such promoters include U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,388,170 (PC1SV promoter), U.S. Pat. No. 6,635,806 (gamma-coixin promoter), and U.S. patent application Ser. No. 09/757,089 (maize chloroplast aldolase promoter). Additional promoters that may find use are a nopaline synthase (NOS) promoter (Ebert et al., 1987), the octopine synthase (OCS) promoter (which is carried on tumor-inducing plasmids of Agrobacterium tumefaciens), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987), the sucrose synthase promoter (Yang et al., 1990), the R gene complex promoter (Chandler et al., 1989), the chlorophyll a/b binding protein gene promoter, CaMV35S (U.S. Pat. Nos. 5,322,938; 5,352,605; 5,359,142; and 5,530,196), FMV35S (U.S. Pat. Nos. 6,051,753; 5,378,619), a PC1SV promoter (U.S. Pat. No. 5,850,019; or SEQ ID NO:20), the SCP promoter (U.S. Pat. No. 6,677,503), and AGRtu.nos (GenBank Accession V00087; Depicker et al, 1982; Bevan et al., 1983) promoters, and the like (see also see Table 1).

Benefit may be obtained for the expression of herbicide tolerance genes by use of a sequence coding for a transit peptide. For example, incorporation of a suitable chloroplast transit peptide, such as, the Arabidopsis thaliana EPSPS CTP (Klee et al., 1987), and the Petunia hybrida EPSPS CTP (della-Cioppa et al., 1986) has been shown to target heterologous EPSPS protein sequences to chloroplasts in transgenic plants. Chloroplast transit peptides (CTPs) are engineered to be fused to the N-terminus of a protein to direct the protein into the plant chloroplast. Such sequences may find use in connection with a nucleic acid conferring dicamba tolerance in particular. Many chloroplast-localized proteins are expressed from nuclear genes as precursors and are targeted to the chloroplast by a chloroplast transit peptide that is removed during the import process. Examples of chloroplast proteins include the small subunit (RbcS2) of ribulose-1,5,-bisphosphate carboxylase, ferredoxin, ferredoxin oxidoreductase, the light-harvesting complex protein I and protein II, and thioredoxin F. Other exemplary chloroplast targeting sequences include the maize cab-m7 signal sequence (Becker et al., 1992; PCT WO 97/41228), the pea glutathione reductase signal sequence (Creissen et al., 1995; PCT WO 97/41228), and the CTP of the Nicotiana tabacum ribulose 1,5-bisphosphate carboxylase small subunit chloroplast transit peptide (SSU-CTP) (Mazur, et al., 1985). Use of AtRbcS4 (CTP1; U.S. Pat. No. 5,728,925), AtShkG (CTP2; Klee et al., 1987), AtShkGZm (CTP2synthetic; see SEQ ID NO:14 of WO04009761), and PsRbcS (Coruzzi et al., 1984), as well as others disclosed, for instance, in U.S. Provisional Patent Application 60/891,675, peptide and nucleic acid sequences for which are listed herein at SEQ ID NOs:21-32, may be of benefit for use with the invention.

A 5' UTR that functions as a translation leader sequence is a DNA genetic element located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, plant rubisco leaders, among others (Turner and Foster, 1995). Non-limiting examples of 5' UTRs that may in particular be of benefit for use GmHsp (U.S. Pat. No. 5,659,122), PhDnaK (U.S. Pat. No. 5,362,865), AtAnt1, TEV (Carrington and Freed, 1990), and AGRtunos (GenBank Accession V00087; Bevan et al., 1983).

The 3' non-translated sequence, 3' transcription termination region, or poly adenylation region means a DNA molecule linked to and located downstream of a structural polynucleotide molecule and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. An example of a 3' transcription termination region is the nopaline synthase 3' region (nos 3'; Fraley et al., 1983). The use of different 3' nontranslated regions is exemplified (Ingelbrecht et al., 1989). Polyadenylation molecules from a Pisum sativum RbcS2 gene (Ps.RbcS2-E9; Coruzzi et al., 1984) and AGRtu.nos (Rojiyaa et al., 1987, Genbank Accession E01312) in particular may be of benefit for use with the invention.

Intron sequences are known in the art to aid in the expression of transgenes in monocot plant cells. Examples of introns include the corn actin intron (U.S. Pat. No. 5,641,876), the corn HSP70 intron (ZmHSP70; U.S. Pat. No. 5,859,347; U.S. Pat. No. 5,424,412), and rice TPI intron (OsTPI; U.S. Pat. No. 7,132,528), and are of benefit in practicing this invention.

Any of the techniques known in the art for introduction of transgenes into plants may be used to prepare a herbicide tolerant plant in accordance with the invention (see, for example, Miki et al., 1993). Suitable methods for transformation of plants are believed to include virtually any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; Agrobacterium-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, etc. Through the application of techniques such as these, the cells of virtually any plant species may be stably transformed, and these cells developed into transgenic plants. Techniques that may be particularly useful in the context of cotton transformation are disclosed in U.S. Pat. Nos. 5,846,797, 5,159,135, 5,004,863, and 6,624,344; and techniques for transforming Brassica plants in particular are disclosed, for example, in U.S. Pat. No. 5,750,871; and techniques for transforming soybean are disclosed in for example in Zhang et al., 1999 and U.S. Pat. No. 6,384,301). Corn can be transformed using methods described in WO9506722 and US patent application 20040244075.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, any suitable plant tissue culture media, for example, MS and N6 media may be modified by including further substances such as growth regulators. Tissue may be maintained on a basic media with growth regulators until sufficient tissue is available to begin plant regeneration efforts, or following repeated rounds of manual selection, until the morphology of the tissue is suitable for regeneration, typically at least 2 weeks, then transferred to media conducive to shoot formation. Cultures are transferred periodically until sufficient shoot formation has occurred. Once shoot are formed, they are transferred to media conducive to root formation. Once sufficient roots are formed, plants can be transferred to soil for further growth and maturity.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct prepared in accordance with the invention. A "transgenic plant" may thus be of any generation. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

The preparation of herbicide compositions for use in connection with the current invention will be apparent to those of skill in the art in view of the disclosure. Such compositions, which are commercially available, will typically include, in addition to the active ingredient, components such as surfactants, solid or liquid carriers, solvents and binders. Examples of surfactants that may be used for application to plants include the alkali metal, alkaline earth metal or ammonium salts of aromatic sulfonic acids, e.g., ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or mixtures of these. Common practice in the case of surfactant use is about 0.25% to 1.0% by weight, and more commonly about 0.25% to 0.5% by weight.

Compositions for application to plants may be solid or liquid. Where solid compositions are used, it may be desired to include one or more carrier materials with the active compound. Examples of carriers include mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or mixtures of these.

For liquid solutions, water-soluble compounds or salts may be included, such as sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate.

Other exemplary components in herbicidal compositions include binders such as polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or mixtures of these; lubricants such as magnesium stearate, sodium stearate, talc or polyethylene glycol, or mixtures of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or mixtures of these.

Equipment and methods known in the art are used to apply various herbicide treatments as disclosed herein. The application rates of herbicides maybe varied, for instance as described above, depending upon the soil texture, pH, organic matter content, tillage systems, and the size of the weed, and can be determined by consulting the herbicide label for the proper herbicide rate.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Tolerance of Soybean Plants Containing DMO-Encoding Polynucleotide Construct to Early Pre-Emergence Application of Dicamba Transgenic soybean plants were obtained by Agrobacterium transformation of soybean cotyledonary nodes using standard procedures and a binary vector containing the DMO-encoding polynucleotide given as SEQ ID NO:7, which encodes the polypeptide of SEQ ID NO:8. Four transgenic soybean events were prepared and designated Events 1-4. Transgenic soybean plants containing the events were tested for their tolerance to dicamba herbicide relative to controls, confirming herbicide tolerance. Non-transgenic soybean plants were used as controls.

Transgenic and control soybean seeds were planted into 3.5-inch square plastic pots containing Redi-earth™ (Scotts-Sierra Horticultural Products Co., Marysville, Ohio). The soil surface was treated with various amounts (561 to 5040 g/ha, 0.5 to 4.5 lb/acre, or 1× to 9× labeled rates) of dicamba formulations (Clarity™ or Banvel™, BASF, Raleigh, N.C.). The pots were placed on capillary matting in 35 inch×60 inch fiberglass watering trays for overhead and/or sub-irrigation for the duration of the test period so as to maintain optimum soil moisture for plant growth and were fertilized with Osmocote (14-14-14 slow release; Scotts-Sierra Horticultural Products Co., Marysville, Ohio) at the rate of 100 gm/cu.ft. to sustain plant growth for the duration of greenhouse trials.

The plants were grown in greenhouses at 27°/21° C. day/night temperature with relative humidity between 25%-75% to simulate warm season growing conditions of late spring. A 14 h minimum photoperiod was provided with supplemental light at about 600 μE as needed. Trials were established in a randomized block design randomized by rate with 4 to 6 replications of each treatment depending on plant quality, availability, and to account for any environmental variability that may have occurred within the confines of each greenhouse.

Treated plants in greenhouse trials were visually assessed at a particular day after treatment (DAT) for injury on a scale of 0 to 100 percent relative to untreated control plants, with zero representing "no" injury and 100% representing "complete" injury or death. Data were collected and analyzed using suitable statistical methods.

The results of the study surprisingly showed that soybean plants transformed with the DMO-encoding polynucleotide construct were tolerant to even early pre-emergence application of dicamba. As indicated in Table 1 below, injury to the transgenic plants was less than 10% even at the highest application rate i.e., 5040 g/ha, 4.5 lb/acre, or 9× labeled rates of dicamba.

TABLE 1

Percentage injury to non-transgenic or transgenic soybean plants from early pre-emergence application of dicamba at sowing. The % injury was represented as ANOVA mean comparisons. Similar letters represent no statistical difference at the p = 0.05 level.

| Formulation Clarity ™ | ID | % injury at shown rates (g ae/ha*) at 14 DAT 561 | 840 | 2244 | 4485 | 5040 |
|---|---|---|---|---|---|---|
| | Control | 67.0 a | 73.0 b | 96.6 a | 98.2 a | 99.5 a |
| | Control | 61.0 a | 86.0 a | 98.1 a | 98.3 a | 99.8 a |
| | Event 1 | 0.0 b | 0.0 c | 1.7 bc | 0.7 b | 3.1 b |
| | Event 2 | 0.0 b | 0.0 c | 1.1 c | 1.0 b | 2.2 b |
| | Event 3 | 0.0 b | 0.0 c | 1.1 c | 0.6 b | 3.5 b |
| | Event 4 | 0.0 b | 0.0 c | 4.4 b | 0.8 b | 7.2 b |
| | LSD | 9.9 | 7.2 | 3.2 | 2.2 | 5.1 |

Example 2

Tolerance of Soybean Plants Containing a DMO-Encoding Polynucleotide Construct to Early Pre-Emergence Application of Dicamba at Sowing Followed by Post-Emergence Application of Dicamba In addition to the method described in Example 2 for early pre-emergence (at sowing) application of dicamba, postemergence (V2 stage of soybean development) application of dicamba was made with a track sprayer using the Teejet 9501E flat fan nozzle (Spraying Systems Co, Wheaton, Ill.) with the air pressure set at a minimum of 24 psi (165 kpa). The spray nozzle was kept at a height of about 16 inches above the top of the plant material for spraying. The spray volume was 10 gallons per acre or 93 liters per hectare.

As shown in Table 2, soybean plants transformed with the DMO-encoding polynucleotide construct were tolerant to early pre-emergence applications of dicamba at sowing followed by post-emergence application of dicamba. Surprisingly, injury to transgenic plants was less than 20% at the overall dicamba rate of 10080 g/ha, 9 lb/acre or 18× labeled rate.

TABLE 2

Percentage injury to non-transgenic or transgenic soybean plants from application of dicamba at sowing followed by post-emergence application at V2 stage.*

| Formulation | | % injury at shown rates (g ae/ha*) at 28 DAT | | | | |
|---|---|---|---|---|---|---|
| Clarity ™ | Plants | 1122 | 1680 | 4488 | 8970 | 10080 |
| | Control | 97.5 a | 98.8 a | 99.8 a | 100.0 a | 100.0 a |
| | Control | 95.6 a | 98.1 a | 99.4 a | 100.0 a | 100.0 a |
| | Event 1 | 0.0 c | 1.8 b | 4.5 d | 11.9 c | 16.9 b |
| | Event 2 | 2.6 bc | 3.9 b | 8.1 bc | 13.8 b | 16.9 b |
| | Event 3 | 3.1 b | 2.9 b | 8.8 b | 11.9 c | 17.5 b |
| | Event 4 | 2.3 bc | 2.0 b | 6.9 c | 11.9 c | 15.6 b |
| | LSD | 3.1 | 2.2 | 1.4 | 1.6 | 1.9 |

*The % injury was represented as ANOVA mean comparisons. Similar letters represent no statistical difference at the p = 0.05 level.

Example 3

Tolerance of Soybean Plants Containing DMO-Encoding Polynucleotide Construct to Late Pre-Emergence Application of Dicamba An analysis was carried out of the effect of late pre-emergence applications of dicamba at soil cracking due to emergence of soybean seedling hypocotyls. Dicamba applications were made using a track sprayer as described in the previous examples. As shown in Table 3, soybean plants transformed with the DMO-encoding polynucleotide construct were found to be tolerant to late pre-emergence application of dicamba at soil cracking. Significantly, injury in the transgenic events was less than 5% even at the highest rate i.e., 5040 g/ha, 4.5 lb/acre, or 9× labeled rates of dicamba.

TABLE 3

Percentage injury to non-transgenic or transgenic soybean plants from late pre-emergence application of dicamba at soil cracking.*

| Formulation | | % injury at shown rates (g ae/ha*) at 14 DAT | | | | |
|---|---|---|---|---|---|---|
| Clarity ™ | Plants | 561 | 840 | 2244 | 4485 | 5040 |
| | Control | 86.9 a | 96.8 a | 98.4 A | 98.5 a | 99.2 a |
| | Control | 89.6 a | 91.9 a | 98.4 A | 99.0 a | 99.4 a |
| | Event 1 | 0.0 b | 0.0 b | 0.5 C | 2.5 bc | 2.0 b |
| | Event 2 | 0.0 b | 0.0 b | 2.9 bc | 0.0 c | 1.5 b |
| | Event 3 | 0.0 b | 0.0 b | 1.5 bc | 4.4 b | 1.3 b |
| | Event 4 | 0.0 b | 0.5 b | 3.3 B | 3.0 bc | 1.3 b |
| | LSD | 8.1 | 5.4 | 2.4 | 3.9 | 2.3 |

*The % injury was represented as ANOVA mean comparisons. Similar letters represent no statistical difference at the p = 0.05 level.

Example 4

Tolerance of Soybean Plants Containing DMO-Encoding Polynucleotide Construct to Late Pre-Emergence Applications of Dicamba Followed by Post-Emergence Applications of Dicamba In addition to the studies above, an analysis was carried out of the effect of late pre-emergence applications of dicamba at soil cracking followed by post-emergence application of dicamba at the V2 stage of development. As shown in Table 4, soybean plants transformed with the DMO-encoding polynucleotide construct were tolerant to late pre-emergence application of dicamba at soil cracking and post-emergence application of dicamba. Injury to transgenic events was less than 20% even at the overall dicamba rate of 10080 g/ha, 9 lb/acre, or 18× labeled rate.

TABLE 4

Percentage injury to non-transgenic or transgenic soybean plants from late pre-emergence application of dicamba at soil cracking followed by post-emergence application at V2 stage.*

| Formulation | | % injury at shown rates (g ae/ha*) at 28 DAT | | | | |
|---|---|---|---|---|---|---|
| Clarity ™ | Plants | 1122 | 1680 | 4488 | 8970 | 10080 |
| | Control | 95.6 a | 98.1 a | 100.0 a | 100.0 a | 100.0 a |
| | Control | 95.0 a | 98.1 a | 99.4 a | 99.8 a | 100.0 a |
| | Event 1 | 0.3 b | 0.9 b | 6.3 b | 13.1 b | 16.3 bc |
| | Event 2 | 0.8 b | 1.6 b | 6.0 b | 11.3 c | 15.0 c |
| | Event 3 | 1.0 b | 1.4 b | 7.5 b | 11.3 c | 17.5 b |
| | Event 4 | 1.8 b | 1.8 b | 7.5 b | 13.1 b | 16.3 bc |
| | LSD | 4.5 | 2.7 | 1.6 | 1.6 | 1.9 |

*The % injury was represented as ANOVA mean comparisons. Similar letters represent no statistical difference at the p = 0.05 level.

Example 5

Tolerance of Soybean Plants Containing DMO-Encoding Polynucleotide Construct to Pre- and Post-Emergence Application of Dicamba in the Field Non-transgenic and transgenic soybean seeds were planted around the beginning of the growing season at the time of optimum growth conditions depending on soil moisture, temperature, and seeding depth. Across all locations seeds were planted under split-plot design with dicamba treatments as whole-plot effects and events as split-plot effects. The design details were as follows: 6 locations, 2 replications/location, 2 rows/plot, row length 12 feet (+3 ft alley), 9 seeds/foot, 108 seeds/row, 5 events (Events 1-4 and a fifth event that was segregating); and 4 treatments as shown below in Table 5. In all 240 plots were planted at 6 locations (40 per location).

TABLE 5

Details of 4 treatments applied to show the tolerance of transgenic soybean to dicamba.

| | 1st Application | | 2nd Application | |
|---|---|---|---|---|
| Treatment | Rate | Plant Stage | Rate | Plant Stage |
| 1 | NO Dicamba | NO Dicamba | NO Dicamba | NO Dicamba |
| 2 | 1.5 lb ae/acre | At Planting | N/A | N/A |
| 3 | N/A | N/A | 1.5 lb ae/acre | V3-4 |
| 4 | 1.5 lb ae/acre | At Planting | 1.5 lb ae/acre | V3-4 |

Four non-transgenic border rows were planted all around the trial using a known commercial line such as A3525. Optimum production and management practices known in the art were followed. Maximum pest control and disease control was practiced as needed to prevent confounding effects of dicamba applications. The field was irrigated as needed according to standard practices.

All plants in the field were treated with pre-emergence and post-emergence applications of dicamba and visually assessed at a particular day after planting for injury on a scale of 0 to 100 percent relative to untreated control plants, with zero representing "no" injury and 100% representing "complete" injury or death. Seed planting and pre-emergence treatment were carried out approximately one-month apart in late spring in Monmouth, Ill. As shown in Table 6, it was found that all transgenic soybean plants had no or very little injury. A fifth transgenic event used appeared to be segregating, so a certain percentage of plants died after the treatments.

TABLE 6

Tolerance of soybean plants containing DMO-encoding polynucleotide construct to pre- and post-emergence application of dicamba in field.*

| Event # | Trmt | % Inj 6/7 | % Inj 6/13 | % Inj 6/20 | % Inj 6/27 | % GR 6/27 | % Inj 7/5 | % GR 7/5 | Dead or Stunted |
|---|---|---|---|---|---|---|---|---|---|
| 1 | No spray | 0 | 0 | 0 | 0 | 0 | 2 | 0 | 0 |
| 1 | No spray | 0 | 0 | 0 | 0 | 0 | 0 | 0 | 0 |
| 2 | No spray | 0 | 0 | 0 | 1 | 0 | 3 | 3 | 0 |
| 2 | No spray | 0 | 0 | 0 | 0 | 0 | 0 | 0 | 0 |
| 3 | No spray | 0 | 0 | 0 | 1 | 0 | 3 | 0 | 0 |
| 3 | No spray | 0 | 0 | 0 | 0 | 0 | 3 | 0 | 0 |
| 4 | No spray | 0 | 0 | 0 | 2 | 0 | 0 | 0 | 0 |
| 4 | No spray | 0 | 0 | 0 | 0 | 0 | 5 | 0 | 0 |
| 5 | No spray | 0 | 0 | 0 | 7 | 0 | 5 | 2 | 0 |
| 5 | No spray | 0 | 0 | 0 | 7 | 3 | 7 | 3 | 0 |
| 1 | Pre at sowing | 0 | 0 | 0 | 1 | 0 | 0 | 0 | 0 |
| 1 | Pre at sowing | 0 | 2 | 0 | 2 | 0 | 0 | 0 | 0 |
| 2 | Pre at sowing | 0 | 0 | 0 | 5 | 0 | 0 | 0 | 0 |
| 2 | Pre at sowing | 0 | 0 | 0 | 2 | 0 | 0 | 0 | 0 |
| 3 | Pre at sowing | 0 | 4 | 0 | 1 | 0 | 0 | 0 | 0 |
| 3 | Pre at sowing | 0 | 2 | 0 | 5 | 0 | 3 | 0 | 0 |
| 4 | Pre at sowing | 0 | 3 | 0 | 5 | 0 | 0 | 0 | 0 |
| 4 | Pre at sowing | 0 | 4 | 0 | 2 | 0 | 0 | 0 | 0 |
| 5 | Pre at sowing | 0 | 15 | 15 | 5 | 0 | 0 | 0 | 24 |
| 5 | Pre at sowing | 0 | 8 | 10 | 2 | 0 | 0 | 0 | 14 |
| 1 | Post at V3 | 0 | 0 | 0 | 5 | 0 | 0 | 0 | 0 |
| 1 | Post at V3 | 0 | 0 | 0 | 7 | 0 | 0 | 0 | 2 |
| 2 | Post at V3 | 0 | 0 | 0 | 3 | 0 | 0 | 0 | 0 |
| 2 | Post at V3 | 0 | 0 | 0 | 3 | 0 | 2 | 0 | 1 |
| 3 | Post at V3 | 0 | 0 | 0 | 3 | 3 | 0 | 0 | 0 |
| 3 | Post at V3 | 0 | 0 | 0 | 5 | 0 | 3 | 0 | 0 |
| 4 | Post at V3 | 0 | 0 | 0 | 3 | 0 | 0 | 0 | 0 |
| 4 | Post at V3 | 0 | 0 | 0 | 3 | 0 | 0 | 0 | 0 |
| 5 | Post at V3 | 0 | 0 | 0 | 7 | 0 | 2 | 0 | 15 |
| 5 | Post at V3 | 0 | 0 | 0 | 5 | 5 | 2 | 0 | 15 |
| 1 | Pre & Post | 0 | 0 | 0 | 5 | 0 | 0 | 0 | 3 |
| 1 | Pre & Post | 0 | 2 | 2 | 5 | 3 | 0 | 0 | 0 |
| 2 | Pre & Post | 0 | 0 | 0 | 1 | 0 | 2 | 0 | 0 |
| 2 | Pre & Post | 0 | 0 | 0 | 2 | 0 | 0 | 0 | 0 |
| 3 | Pre & Post | 0 | 0 | 0 | 3 | 0 | 2 | 0 | 0 |
| 3 | Pre & Post | 0 | 2 | 0 | 3 | 0 | 0 | 0 | 0 |
| 4 | Pre & Post | 0 | 0 | 0 | 3 | 8 | 2 | 2 | 0 |
| 4 | Pre & Post | 0 | 1 | 0 | 3 | 3 | 0 | 0 | 0 |
| 5 | Pre & Post | 0 | 15 | 10 | 3 | 5 | 0 | 0 | 23 |
| 5 | Pre & Post | 0 | 10 | 10 | 1 | 0 | 0 | 0 | 20 |

*No spray means no dicamba was applied to the plants.

Pre at sowing means 1.5 lb/acre of dicamba was applied at planting.

Post at V3 means 1.5 lb/acre of dicamba was applied 4 weeks after planting.

Pre and post means 1.5 lb/acre of dicamba was applied at planting and 1.5 lb/acre of dicamba was applied 4 weeks after planting.

% inj means percentage injury on given date.

% GR means percentage growth reduction.

Example 6

Controlling Glyphosate Tolerant Weeds by Dicamba

Marestail is one of the major weeds in a crop field. Marestail is effectively controlled by glyphosate, but the development of methods for controlling this common weed with other herbicides is important to minimize opportunities for herbicide tolerance to develop. An analysis was carried out to determine the extent to which this glyphosate tolerant weed could be controlled by applications of dicamba. Marestail (Conyza canadensis) plants of two biotypes, each from a different geographic region, California (CA) and Kentucky (KY), were grown, and treated at 4-6 inch diameter rosette leaf stage with dicamba as described in Example 2 and 3. The results of the study, as shown in Table 7, demonstrated that dicamba was equally effective in controlling both susceptible and tolerant biotypes of marestail from CA and KY. Dicamba was more effective in controlling resistant biotypes at lower application rates than glyphosate. For example, 2100 g/ha of glyphosate was required to obtain about 77% and 91% inhibition of CA and KY resistant biotypes, whereas only 280 g/ha of dicamba was required to obtain about 83% and about 91% control of CA and KY resistant biotypes.

TABLE 7

Control of glyphosate tolerant weeds by dicamba.

| Formulation | Rate g/ha | % Injury (21 DAT) MARESTAIL (CA) Susceptible | MARESTAIL (CA) Resistant | MARESTAIL (KY) Susceptible | MARESTAIL (KY) Resistant |
|---|---|---|---|---|---|
| Roundup WeatherMAX ™ | 840 | 97.2 | 55.0 | 76.7 | 58.3 |
| | 1680 | 100.0 | 64.2 | 97.5 | 79.2 |
| | 2100 | 100.0 | 76.7 | 100.0 | 90.8 |
| Clarity ™ | 50 | 68.3 | 61.7 | 78.3 | 78.3 |
| | 140 | 82.5 | 80.8 | 90.0 | 88.3 |
| | 280 | 85.0 | 82.5 | 91.7 | 90.8 |

Example 7

Development of a Method for Controlling Glyphosate Tolerant Weeds in a Field Transgenic seeds having dicamba tolerance are planted in a field that has been treated with glyphosate before planting the transgenic seeds. The field is then treated with a herbicidally effective amount of dicamba before or after planting the seeds to control glyphosate resistant weeds. The herbicidally effective amount of dicamba is such that the growth of glyphosate resistant weeds is controlled, but is not injurious to the planted crop as shown in the examples described herein. Thus, transgenic seeds having dicamba tolerance in combination with an effective amount of dicamba are useful for control of glyphosate resistant weeds. The method may be implemented without delaying planting of the dicamba tolerant crop plants, thus providing a significant advance over the prior art, in which dicamba must be applied sufficiently prior to planting such that the dicamba degrades in the environment sufficiently to avoid injury to crop plants.

Example 8

Combination of Dicamba and Glyphosate for Controlling Glyphosate Resistant Weeds to Allow Reduced Herbicide Application Rates As shown in Table 8, dicamba alone was more effective in controlling resistant biotypes at lower application rates than glyphosate. Further, it has unexpectedly been found that dicamba in combination with glyphosate allows control of glyphosate tolerant and susceptible weeds at lower application rates. For example, whereas 200 g/ha of glyphosate was able to control only 6% of marestail (KY resistant biotype) at 18 DAT and 40 g/ha of dicamba was able to control about 52% of the KY biotype at 18 DAT, a 200 g/ha glyphosate and 40 g/ha dicamba mixture was able to control about 79% of the KY biotype at 18 DAT.

In general, any formulation containing dicamba appeared to be more efficacious than glyphosate alone on the resistant biotype. Also, in general, the following trend in effectiveness of glyphosate to dicamba ratio on resistant biotype was found to be true at: 4:1>10:1>20:1>40:1>80:1. The results show that a glyphosate to dicamba mixture ratio of 4:1 containing 200 g/h glyphosate and 50 g/h dicamba provided superior control than either glyphosate or dicamba alone.

TABLE 8

Effect of dicamba and glyphosate for controlling glyphosate resistant weeds.

| CHEMICAL FORMULATION | Rate g/ha | RATIO | % Injury (18 DAT) Marestail Susceptible (KY) | Marestail Resistant (KY) | % Injury (30 DAT) Marestail Susceptible (KY) | Marestail Resistant (KY) |
|---|---|---|---|---|---|---|
| Roundup | 200 | | 86.0 | 5.8 | 96.3 | 0.0 |
| WeatherMAX ™ | 400 | | 99.7 | 25.0 | 100.0 | 18.3 |
| | 800 | | 100.0 | 46.7 | 100.0 | 44.2 |
| | 1600 | | 100.0 | 59.2 | 100.0 | 62.5 |
| Clarity ™ | 2.5 | | 6.7 | 10.8 | 15.8 | 7.5 |
| | 5 | | 18.3 | 25.0 | 20.8 | 35.0 |
| | 10 | | 34.2 | 35.8 | 29.2 | 39.2 |
| | 20 | | 40.8 | 45.8 | 40.0 | 45.0 |
| | 40 | | 50.0 | 52.5 | 51.7 | 68.3 |
| | 80 | | 68.3 | 69.2 | 71.7 | 84.3 |
| | 100 | | 83.3 | 75.8 | 86.3 | 87.5 |
| | 200 | | 89.2 | 83.3 | 99.3 | 94.3 |
| Roundup | 200 + 2.5 | 80:1 | 50.8 | 20.8 | 55.8 | 31.7 |
| WeatherMAX ™ + | 400 + 5 | 80:1 | 85.8 | 39.2 | 97.7 | 40.8 |
| Clarity ™ | 800 + 10 | 80:1 | 99.7 | 47.5 | 100.0 | 45.0 |
| | 1600 + 20 | 80:1 | 100.0 | 50.8 | 100.0 | 63.3 |
| Roundup | 200 + 5 | 40:1 | 56.7 | 28.3 | 64.2 | 35.0 |
| WeatherMAX ™ + | 400 + 10 | 40:1 | 82.5 | 40.0 | 94.2 | 43.3 |
| Clarity ™ | 800 + 20 | 40:1 | 99.3 | 53.3 | 100.0 | 60.8 |
| | 1600 + 40 | 40:1 | 100.0 | 70.8 | 100.0 | 80.8 |

TABLE 8-continued

Effect of dicamba and glyphosate for controlling glyphosate resistant weeds.

| CHEMICAL FORMULATION | Rate g/ha | RATIO | % Injury (18 DAT) Marestail Susceptible (KY) | % Injury (18 DAT) Marestail Resistant (KY) | % Injury (30 DAT) Marestail Susceptible (KY) | % Injury (30 DAT) Marestail Resistant (KY) |
|---|---|---|---|---|---|---|
| Roundup | 200 + 10 | 20:1 | 58.3 | 38.3 | 66.7 | 40.0 |
| WeatherMAX ™ + | 400 + 20 | 20:1 | 81.7 | 56.7 | 93.3 | 50.0 |
| Clarity ™ | 800 + 40 | 20:1 | 99.0 | 62.5 | 100.0 | 73.3 |
| | 1600 + 80 | 20:1 | 99.7 | 77.5 | 100.0 | 88.3 |
| Roundup | 200 + 20 | 10:1 | 56.7 | 52.5 | 70.8 | 60.0 |
| WeatherMAX ™ + | 400 + 40 | 10:1 | 84.2 | 79.2 | 93.3 | 86.3 |
| Clarity ™ | 800 + 80 | 10:1 | 98.7 | 83.3 | 100.0 | 96.8 |
| | 1600 + 160 | 10:1 | 99.7 | 89.2 | 100.0 | 99.3 |
| Roundup | 200 + 50 | 4:1 | 61.7 | 79.2 | 83.5 | 87.2 |
| WeatherMAX ™ + | 400 + 100 | 4:1 | 89.2 | 88.3 | 99.7 | 98.7 |
| Clarity ™ | 800 + 200 | 4:1 | 99.7 | 88.3 | 100.0 | 99.3 |
| | 1600 + 400 | 4:1 | 100.0 | 89.7 | 100.0 | 100.0 |

Example 9

Production of Transgenic Seeds Having Dicamba and Glyphosate Tolerance

Methods for producing transgenic seeds having glyphosate tolerance are known in the art and such seeds can be produced by persons of skill in the art by using a polynucleotide encoding glyphosate resistant 5-enolpyruvylshikimate-3-phosphate synthase (EPSPS) as described in U.S. Pat. Nos. 5,627,061, 5,633,435, 6,040,497 and in U.S. Pat. No. 5,094,945, WO04074443 and WO04009761, all of which are hereby incorporated by reference. Soybean breeding lines containing the Roundup Ready® trait event 40-3-2 (Padgette et al., 1995) have been produced. Seeds from soybean plant designated as MON19788 have been deposited under ATCC Accession No. PTA-6708.

Glyphosate tolerant plants can also be produced by incorporating polynucleotides encoding glyphosate degrading enzymes such as glyphosate oxidoreductase (GOX, U.S. Pat. No. 5,463,175, herein incorporated by reference), a glyphosate-N-acetyl transferase (GAT, U.S. Patent publication 20030083480, herein incorporated by reference), and a glyphosate decarboxylase (WO05003362; US Patent Application 20040177399, herein incorporated by reference).

Dicamba tolerant plants are disclosed herein. A suitable line from each is crossed and progeny seeds screened with herbicide applications of glyphosate and dicamba to obtain progeny expressing both genes and exhibiting tolerance to both dicamba and glyphosate. Alternatively, coding sequences conferring tolerance to one or both of the herbicides are directly introduced into a given line. Seeds from these plants are used for developing a method for controlling weed resistance development in a field as described below.

Transgenic seeds having dicamba and glyphosate tolerances were tested for their tolerance to dicamba, glyphosate, or both herbicides. Table 9 shows tolerance of transgenic soybeans carrying glyphosate and dicamba tolerance transgenes to glyphosate, dicamba, and glyphosate and dicamba at various stages of plant growth. Injury was not seen on plants when either or both herbicides were applied at pre-emergence stage. Post-emergence treatments of either or both herbicides at V3, R1, and R3-4 showed only little injury.

TABLE 9

Tolerance of transgenic soybeans carrying glyphosate and dicamba tolerance transgenes to glyphosate, dicamba, and glyphosate and dicamba.

| Plant Line | Herbicide Applied | Rate gm ae/ha | Pre-emergence treatment 20 DAT | Post-emergence treatment V3 8 DAT | R1 7 DAT | R3-4 18 DAT |
|---|---|---|---|---|---|---|
| | | | % injury (Average of 4 replications) | | | |
| Non-transgenic Control | CLARITY | 561 | 99.0 | 83.8 | 71.3 | 85.0 |
| | RWMax | 841 | 0.0 | 81.3 | 66.3 | 67.5 |
| | CLARITY + RWMax | 561 + 841 | 99.5 | 93.8 | 81.3 | 99.0 |
| RR1+ DMO Line 1 | CLARITY | 561 | 0.0 | 7.0 | 6.3 | 4.5 |
| | RWMax | 841 | 0.0 | 3.5 | 3.5 | 11.3 |
| | CLARITY + RWMax | 561 + 841 | 0.0 | 3.0 | 4.0 | 10.0 |
| RR1+ DMO Line 2 | CLARITY | 561 | 0.0 | 5.3 | 6.3 | 5.3 |
| | RWMax | 841 | 0.0 | 4.5 | 4.5 | 11.7 |
| | CLARITY + RWMax | 561 + 841 | 0.0 | 5.0 | 4.0 | 8.8 |
| RR1+ DMO Line 3 | CLARITY | 561 | 0.0 | 9.0 | 8.8 | 7.5 |
| | RWMax | 841 | 0.0 | 3.5 | 4.0 | 11.3 |
| | CLARITY + RWMax | 561 + 841 | 0.0 | 4.5 | 3.5 | 10.0 |

TABLE 9-continued

Tolerance of transgenic soybeans carrying glyphosate and dicamba tolerance transgenes to glyphosate, dicamba, and glyphosate and dicamba.

| Plant Line | Herbicide Applied | Rate gm ae/ha | Pre-emergence treatment 20 DAT | Post-emergence treatment V3 8 DAT | R1 7 DAT | R3-4 18 DAT |
|---|---|---|---|---|---|---|
| | | | % injury (Average of 4 replications) | | | |
| RR1+ DMO Line 4 | CLARITY | 561 | 0.0 | 8.5 | 8.8 | 3.5 |
| | RWMax | 841 | 0.0 | 3.5 | 3.5 | 11.3 |
| | CLARITY + RWMax | 561 + 841 | 0.0 | 4.5 | 4.5 | 8.8 |
| RR2+ DMO Line 1 | CLARITY | 561 | 0.0 | 8.5 | 6.3 | 5.3 |
| | RWMax | 841 | 0.0 | 3.5 | 3.5 | 3.0 |
| | CLARITY + RWMax | 561 + 841 | 0.0 | 5.0 | 4.5 | 5.0 |
| RR2+ DMO Line 2 | CLARITY | 561 | 0.0 | 9.0 | 6.3 | 3.0 |
| | RWMax | 841 | 0.0 | 3.5 | 6.3 | 3.0 |
| | CLARITY + RWMax | 561 + 841 | 0.0 | 9.5 | 7.0 | 3.0 |
| RR2+ DMO Line 3 | CLARITY | 561 | 0.0 | 9.5 | 7.5 | 3.5 |
| | RWMax | 841 | 0.0 | 3.5 | 6.3 | 4.5 |
| | CLARITY + RWMax | 561 + 841 | 0.0 | 8.5 | 3.5 | 3.3 |
| RR2+ DMO Line 4 | CLARITY | 561 | 0.0 | 5.3 | 5.8 | 3.0 |
| | RWMax | 841 | 0.0 | 16.5 | 17.0 | 4.0 |
| | CLARITY + RWMax | 561 + 841 | 0.0 | 11.0 | 3.5 | 5.3 |

Example 10

Development of a Method for Controlling Weed Resistance Development in a Field Transgenic seeds having dicamba and glyphosate tolerance prepared as described above are planted in a field. The field is treated with dicamba and glyphosate before or after planting the seeds using a mixture of dicamba and glyphosate in an effective amount to control weed growth. Typically about a 1× application rate of either herbicide will be effective in controlling weed growth, but the rate may be varied depending upon environmental conditions and the type of weeds being controlled, as is known in the art. The rate of application may also be increased or decreased depending upon the rate of control desired. Generally speaking, increasing the rate of one herbicide will allow a decrease in the rate of the second herbicide in order to obtain the same level of seed control. In specific embodiments, an application of from about 200 to about 1600 g/ha of glyphosate is combined with from about 20 to about 400 g/ha of dicamba.

A desired application rate may be optimized in any particular environment or in the context of a particular weed can be determined using the experimental layout of Example 9 with the different formulation rates described therein. In addition to desired level of weed control, the herbicide level is selected to avoid using more herbicide than is needed on the one hand, and to avoid poor weed control that could lead to herbicide tolerant plants. Over application of herbicides could also damage herbicide tolerant crop. As shown in Example 9 above however, combining optimized applications of these herbicides provides significant levels of control of even herbicide tolerant weeds, and thus represents a major advance in the art.

Example 11

Development of a Method for Controlling Weeds in a Single Pass in a Field

The procedures in Examples 9 and 10 are applied to develop a method for controlling weed growth in a crop-growing environment involving planting a transgenic seed in a field containing a weed or a seed thereof and treating the field in a single pass though the field. The treatment comprises a herbicidally effective amount of dicamba, glyphosate, or a mixture thereof, administered contemporaneously with the planting of the seed. The planting, treating, and growing of the transgenic seed are achieved by standard agricultural methods.

Such a method of planting the transgenic seed and treating the transgenic seed in one pass eliminates the need for a farmer to make multiple passes through the field, including once for planting and once for spraying. The technique therefore reduces fuel and wear-tear costs to farmers.

Example 12

Tolerance of Plants Containing DMO-Encoding Polynucleotide Molecule to Other Auxin-Like Herbicides Herbicide drift and contamination of herbicide delivery equipment is a serious concern in agriculture and can injure non-target crops resulting in losses to farmers. However, some level of drift is often inevitable due to changing environmental conditions such as wind and the proximity of growing fields. Further, it is often difficult and expensive to eliminate all residual levels of a herbicide in a tank following herbicide application and residual herbicides often result in inadvertent injury to crops. Often several rinses of herbicide delivery equipment are required before it can be used for another herbicide, which wastes water and cleaning chemicals.

As herbicides such as 2,4-D and MCPA are post-emergent herbicides for some crops, but can cause serious damage to non-target crops, residual contamination with these herbicides is of particular concern. A transgenic crop tolerant to at least low levels of these herbicides would therefore be of significant value in managing injuries due to spray drift and contamination of herbicide equipment. This could also reduce the extent of equipment washing needed for herbicide delivery equipment.

An analysis was therefore carried out to determine whether soybean plants having DMO-encoding polynucleotide could deactivate other auxin-like herbicides in addition to dicamba, including 2,4-D and MCPA. This was carried out by applying various concentrations of commercially available formulations of other auxin-like herbicides such as 2,4-D (Helena, Collierville, Tenn.), MCPA (Agriliance, St. Paul, Minn), triclopyr (GARLON 3A; Dow Elanco, Indianapolis, Ind.), clopyralid (STINGER; Dow Elanco, Indianapolis, Ind.), picloram (TORDON 22K; Dow Elanco, Indianapolis, Ind.), or Banvel or CLARITY (BASF, Raleigh, N.C.) to DMO containing plant tissues or plants.

Transgenic soybean plants were obtained by Agrobacterium-mediated transformation of soybean explants with a DMO-encoding polynucleotide as described above for the events designated Events 1-4. A non-transgenic line was used as a control. Non-transgenic and transgenic soybean seeds were planted into 3.5-inch square plastic pots containing Redi-earth™ (Scotts-Sierra Horticultural Products Co., Marysville, Ohio). The pots were placed on capillary matting in 35 inch×60 inch fiberglass watering trays for overhead and/or sub-irrigation for the duration of the test period so as to maintain optimum soil moisture for plant growth. The pots were fertilized with Osmocote (14-14-14 slow release; Scotts-Sierra Horticultural Products Co., Marysville, Ohio) at the rate of 100 gm/cu.ft. to sustain plant growth for the duration of greenhouse trials, and grown in greenhouses at 27°/21° C. day/night temperature, with relative humidity between 25%-75% to simulate warm season growing conditions of late spring. A 14 h minimum photoperiod was provided with supplemental light at about 600 μE as needed.

All herbicide applications were made with the track sprayer using a Teejet 9501E flat fan nozzle (Spraying Systems Co, Wheaton, Ill.) with air pressure set at a minimum of 24 psi (165 kpa). The spray nozzle was kept at a height of about 16 inches above the top of plant material for spraying. The spray volume was 10 gallons per acre or 93 liters per hectare. Applications were made when plants had reached V-3 stage. All trials were established in a randomized block design (randomized by rate) with 4 to 6 replications of each treatment depending on plant quality, availability and to account for any environmental variability that may have occurred within the confines of each greenhouse.

All treated plants in greenhouse trials were visually assessed at about 4, 14, 18, and 21 days after treatment (DAT) for injury on a scale of 0 to 100 percent relative to untreated control plants, with zero representing "no" injury and 100% representing "complete" injury or death. Data were collected using a palm top computer and analyzed using standard statistical methods. The results shown in Table 10 clearly indicate tolerance of transgenic soybean to other auxin-like herbicides such as 2,4-D and MCPA relative to the non-transgenic line.

TABLE 10

Percentage injury relative to un-treated controls at 25 DAT post-V3 applications of different auxin-like herbicides to non-transgenic or transgenic soybean plants.*

| Herbicide | Plant/trial | 280 | 561 | 1120 |
|---|---|---|---|---|
| | | % injury at shown rates (g ae/ha**) at 21 DAT | | |
| Dicamba (Clarity) | Non-transgenic | | 100 | 100 |
| | Event 1 | | 0.0 | 1.2 |
| | Event 2 | | 0.0 | 1.7 |
| | Event 3 | | 0.0 | 0.7 |
| | Event 4 | | 0.0 | 1.5 |

TABLE 10-continued

Percentage injury relative to un-treated controls at 25 DAT post-V3 applications of different auxin-like herbicides to non-transgenic or transgenic soybean plants.*

| Herbicide | Plant/trial | 280 | 561 | 1120 |
|---|---|---|---|---|
| Dicamba (Banvel) | Non-transgenic | | 100.0 | 100.0 |
| | Event 1 | | 0.0 | 1.5 |
| | Event 2 | | 0.0 | 0.7 |
| | Event 3 | | 0.0 | 0.5 |
| | Event 4 | | 0.0 | 1.3 |
| 2,4-D | Non-transgenic | 86.8 | 100.0 | 100.0 |
| | Event 1 | 58.3 | 75.0 | 100.0 |
| | Event 2 | 64.2 | 94.7 | 100.0 |
| | Event 3 | 40.0 | 85.0 | 100.0 |
| | Event 4 | 45.8 | 84.2 | 100.0 |
| MCPA | Non-transgenic | 93.0 | 98.3 | 100.0 |
| | Event 1 | 72.5 | 99.3 | 100.0 |
| | Event 2 | 55.0 | 95.0 | 99.7 |
| | Event 3 | 55.0 | 95.8 | 100.0 |
| | Event 4 | 88.3 | 98.8 | 100.0 |
| | LSD | 16.3 | 10.6 | 3.7 |
| | | % injury shown rates (g ae/ha**) at 14 DAT | | |
| Triclopyr | Non-transgenic | 86.7 | 97.3 | 98.7 |
| | Event 1 | 88.3 | 95.7 | 99.3 |
| | Event 2 | 86.7 | 98.7 | 99.3 |
| | Event 3 | 86.7 | 94.0 | 96.3 |
| | Event 4 | 90.8 | 98.0 | 99.2 |
| Clopyralid | Non-transgenic | 99.3 | 100.0 | 100.0 |
| | Event 1 | 99.2 | 100.0 | 100.0 |
| | Event 2 | 98.2 | 99.7 | 100.0 |
| | Event 3 | 99.3 | 100.0 | 100.0 |
| | Event 4 | 99.7 | 100.0 | 100.0 |
| Picloram | Non-transgenic | 99.3 | 100.0 | 100.0 |
| | Event 1 | 99.7 | 100.0 | 100.0 |
| | Event 2 | 99.3 | 100.0 | 100.0 |
| | Event 3 | 99.3 | 99.7 | 100.0 |
| | Event 4 | 99.3 | 100.0 | 100.0 |
| | | % injury at shown rates (g ae/ha**) at 21 DAT | | |
| | LSD | 2.9 | 1.8 | 1.4 |

*The % injury was represented as ANOVA mean comparisons.

**grams of active acid equivalent/hectare

Another auxin-like herbicide Butyrac 200 (2,4-DB; Albaugh) was also tested on transgenic soybean plants carrying a DMO gene for testing the plants tolerance to it. The herbicide was applied as a post-emergence treatment at three application rates on two transgenic soybean events and compared with a non-transgenic line for total crop injury across all three application rates: 280 g/ha (0.25 lb/a), 561 g/ha (0.5 lb/a) and 841 g/ha (0.75 lb/a) (see Table 11). Both transgenic soybean lines showed low level of tolerance to 2,4-DB. This example shows that dicamba tolerant soybean is also tolerant to low levels of 2,4-DB and should be useful in managing damage from spray drift from the same or neighboring fields to prevent crop loses, and would exhibit tolerance to residual levels of 2,4-DB following incomplete washing of herbicide delivery equipment.

TABLE 11

Percentage injury relative to the untreated control at 16 DAT by the application of 2,4-DB to non-transgenic or transgenic soybean plants.

| Herbicide | Plant | % injury at shown rates (g ae/ha) at 16 DAT | | |
|---|---|---|---|---|
| | | 280 | 561 | 1120 |
| 2,4-DB (Butyrac 200) | | | | |
| | Non-transgenic | 59.2 | 70.0 | 79.2 |
| | NE3001 | | | |
| | 462-1-21 | 25.0 | 43.3 | 75.8 |
| | 469-13-19 | 18.3 | 37.5 | 70.0 |

This example shows that transgenic soybean plants exhibit tolerance to other auxin-like herbicides, indicating a likely common deactivation mechanism for dicamba and other auxin-like herbicides such as 2,4-D and MCPA. In case of triclopyr, clopyralid, and picloram, the application rate of 280 g ae/ha appeared too stringent in this study and thus lower concentrations may be desired in most settings to reduce plant damage. Thus, a DMO polynucleotide containing soybean that is tolerant to dicamba is also tolerant to low levels of 2,4-D and MCPA and should prevent or minimize damage from spray drift from same or neighboring fields to prevent crop loses, and would exhibit tolerance to residual levels of these herbicides following incomplete washing of herbicide delivery equipment. The herbicide delivery equipment could include a tank, container, hose, strainer, boom, sprayer, nozzle, pump, and accessories such as coupling, elbows, shanks, and valves. The delivery equipment is operable manually or mechanically for example on a farm vehicle, airplane, and helicopter, among others.

Example 13

Production of Dicamba Tolerant Transgenic Corn Plants

To test the use of a DMO gene in providing dicamba tolerance to monocots, transgenic corn plants were produced that comprise a DMO gene as disclosed above with or without a transit peptide (e.g. Ta Waxy, CTP1, CTP2synthetic, CTP4) under the control of plant gene expression elements such as a promoter (e.g. PC1SV, e35S, OsAct1, OsTPI, OsAct15), and an intron (e.g. OsAct1, OsAct15, OsTPI, ZmHSP70). This expression element contains first intron and flanking UTR exon sequences from the rice actin 1 gene and includes 12 nt of exon 1 at the 5' end and 7 nt of exon 2 at the 3' end), and a 3'UTR (e.g. TaHsp17). Nucleotide sequences/and or patent references for various expression elements are disclosed in co-pending application U.S. Ser. No. 60/891,675.

Transgenic corn plants were produced by the methods known in the art such as WO9506722 and US patent application 20040244075. Transgenic corn events having single copy were evaluated for dicamba tolerance at a single location replicated trial. Six events from each of the six constructs were used. The experimental design was as follows: rows/entry: 1; treatment: 0.5 lb/a of dicamba at V3 stage followed by 1 lb/a of dicamba at V8 stage (Clarity®, BASF, Raleigh, N.C.); replications: 2; row spacing: 30 inches; plot length: minimum 20 feet; plant density: about 30 plants/17.5 ft.; alleys: 2.5 feet. The entire plot was fertilized uniformly to obtain an agronomically acceptable crop. A soil insecticide such as Force® 3G (Syngenta Crop Protection, Greensboro, N.C., USA) at 5 oz. per 1000 ft. of row for control of corn rootworm was applied at planting time. If black cutworm infestation was observed, POUNCE® 3.2EC at 4 to 8 oz. per acre rate (FMC Corporation, Philadelphia, Pa.) was used. In addition, an insecticide spray program was used to control all above ground lepidopteran pests including European corn borer, corn earworm, and fall armyworm. POUNCE® 3.2EC at 4 to 8 oz. per acre was applied every 3 weeks to control lepidopteran pests; about 4 applications were made. The plot was kept weed free with a pre-emergence application of a herbicide such as Harness® Xtra 5.6 L (Monsanto, St. Louis, Mo.) and Degree Xtra® (Monsanto, St. Louis, Mo.). If weed escapes were observed in the untreated check, they were controlled by hand weeding or a post-emergence application of PERMIT (Monsanto, St. Louis, Mo.) or BUCTRIL® (Bayer, Research Triangle Park, NC) over the entire trial.

Corn inbred lines transformed with DNA constructs comprising a DMO transgene were tested for dicamba tolerance by measuring brace root injury when treated with 0.5 lb/a of dicamba at V3 stage followed by 1 lb/a of dicamba at V8 stage. Brace root injury was evaluated visually by counting the number of plants in a row showing an "atypical" morphology of having the brace roots fused as compared to a typical morphology of "finger-like" structure. As shown in Table 12, corn plants transformed with DNA constructs coding for a DMO without linking it to a CTP (pMON73699, pMON73704) showed higher level of brace root injury, i.e. lower level of protection upon dicamba treatment. The constructs coding for a DMO linked to a CTP (pMON73716, pMON73700, pMON73715, pMON73703) showed lower level of brace root injury, i.e. higher level of protection upon dicamba treatment.

TABLE 12

Percentage brace root injury as a measure of dicamba tolerance exhibited by transgenic corn plants transformed with DNA constructs carrying DMO.

| Inbreds/ Constructs | Details | Brace root injury |
|---|---|---|
| 01CSI6 | Susceptible inbred to dicamba | 95.4 |
| LH244 | Resistant inbred to dicamba | 93.8 |
| pMON73699 | PC1SV/I-OsAct1/DMO-Wmc/TaHsp17 | 93.2 |
| pMON73704 | e35S/I-OsAct1/DMO-Wmc/TaHsp17 | 91.3 |
| pMON73716 | PC1SV/I-OsAct1/TaWaxy/DMO-Wmc/TaHsp17 | 78.8 |
| pMON73700 | PC1SV/I-OsAct1/CTP1/DMO-Wmc/TaHsp17 | 74.4 |
| pMON73715 | PC1SV/I-OsAct1/CTP2syn/DMO-Wmc/TaHsp17 | 68.2 |
| pMON73703 | e35S/I-OsAct1/CTP1/DMO-Wmc/TaHsp17 | 68.8 |

Example 14

Production of Dicamba Tolerant Transgenic Cotton Plants

To test the use of DMO gene in providing dicamba tolerance to cotton, transgenic cotton plants were produced. Several DNA constructs carrying a DMO coding region as disclosed herein with a transit peptide (e.g., PsRbcS CTP, CTP1, CTP2) under the control of plant gene expression elements such as a promoter (e.g. PC1SV, FMV, or e35S), and a 3'UTR (e.g. E6; Accession # U30508) were produced and transformed into cotton (Gossypium hirsutum) as follows. Nucleotide sequences/and or patent references for various expression elements are disclosed in co-pending application U.S. Ser. No. 60/891,675. Media used are noted in Table 13.

Cotton transformation was performed, for instance as described according to U.S. Patent Application Publication 20040087030, via an embryogenic approach. Explants of cotton cv Coker 130 were grown in vitro and with a liquid suspension of Agrobacterium tumefaciens carrying a DNA construct of interest, using selection on kanamycin containing media. Putative transgenic plantlets were then transferred to soil to obtain mature cotton plants. The transgenic nature of transformants was confirmed by DNA testing.

TABLE 13

Composition of various media used for cotton transformation.

| Components | Amount/L | | | | |
|---|---|---|---|---|---|
| | Glucose | Sucrose | UMO | TRP+ | SHSU |
| MS basal salts (Phytotech.) | 4.33 g | 4.33 g | 4.33 g | 4.33 g | — |
| Gamborg's B5 vitamins (Phytotech) (500X) | 2 ml | 2 ml | 2 ml | 2 ml | — |
| 2,4-D (1 mg/ml) | 0.1 ml | 0.1 ml | — | | — |
| Stewart and Hsu majors (10X) | — | — | — | — | 100 ml |
| Stewart and Hsu minors (100X) | — | — | — | — | 10 ml |
| Steward and Hsu organic (100X) | — | — | — | — | 10 ml |
| Kinetin (0.5 mg/ml) | 1 ml | 1 ml | — | — | — |
| Chelated iron (100X) | — | — | — | — | 1.5 ml |
| Glucose | 30 g | 30 g | 30 g | 30 g | 5 g |
| Potassium nitrate | — | — | — | 1.9 g | — |
| Casein hydrolysate | — | — | — | 0.1 g | — |
| pH | 5.8 | 5.8 | 5.8 | 5.8 | 6.8 |
| Phytagel (Sigma) | 2.5 g | 2.5 g | — | — | — |
| Gelrite (Kelco) | — | — | 3.5 g | 3.5 g | 2.2 g |
| Carbenicillin (250 mg/ml) | 1.7 ml | 1.7 ml | 1.7 ml | 1.7 ml | — |
| Cefotaxime (100 mg/ml) | 1 ml | 1 ml | 1 ml | 1 ml | — |
| Benlate (50 mg/ml) | — | — | — | 1 ml | 1 ml |
| Kanamycin (50 mg/ml) | 0.8-1.0 ml | 0.8-1.0 ml | 1 ml | — | — |
| Sucrose | — | 0.1 g | — | — | — |
| Ascorbic acid | — | — | 100 mg | | |

Transformed cotton plants that comprise a DNA construct, i.e, each comprising a different combination of a DMO coding region with a transit peptide, a promoter, and a 3'UTR, were treated with dicamba (Clarity®, BASF, Raleigh, N.C.) as a post-emergent treatment at V4-5 growth stage at the rate of 561 g ae/ha (0.5 lb/a) and found to be tolerant whereas untransformed cotton plants showed an injury rate of 79% to 86%. Transgenic plants showing more than 95% tolerance (equal to less than 5% injury) were selected for further studies. Transgenic plants were also tolerant to a subsequent post-emergent treatment of dicamba. For example, the plants that were treated with 0.5 lb/acre of dicamba at V3-4 stage followed by either 1 or 2 lb/acre of dicamba at V5 or later stages were still tolerant to dicamba. R1 transgenic seeds and plants were also subjected to pre-emergence or pre-emergence and post-emergence dicamba treatment and found to be tolerant. This example shows that a DMO gene can provide dicamba tolerance to cotton at various stages of growth thus enabling application of dicamba at various stages to obtain effective weed control.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. Nos. 4,554,101; 5,004,863; 5,015,580; 5,017,692; 5,094,945; 5,159,135; 5,322,938; 5,352,605; 5,359,142; 5,384,253; 5,424,412; 5,445,962; 5,463,175; 5,508,184; 5,530,196; 5,538,880; 5,550,318; 5,552,299; 5,567,600; 5,567,862; 5,591,616; 5,627,061; 5,633,435; 5,633,437; 5,635,055; 5,641,876; 5,689,052; 5,750,871; 5,824,877; 5,837,848; 5,846,797; 5,859,347; 5,939,602; 5,981,840; 6,040,497; 6,140,078; 6,160,208; 6,175,060; 6,177,611; 6,232,526; 6,252,138; 6,294,714; 6,384,301; 6,388,170; 6,399,861; 6,403,865; 6,414,222; 6,426,446; 6,429,357; 6,429,362; 6,433,252; 6,437,217; 6,613,963; 6,635,806; 6,677,503; 7,132,528

U.S. application Ser. No. 09/757,089

U.S. Patent Appln. Publication 20030083480

U.S. Patent Appln. Publication 20030135879

U.S. Patent Appln. Publication 2004087030

U.S. Patent Appln. Publication 20070079393

U.S. Provisional Patent Appl. Ser. No. 60/891,675

Anonymous, Greenbook Crop Protection Reference, 23rd edition, Greenbook Products, Lenexa, Kans., 2007.

Becker et al., Plant Mol. Biol., 20(1):49-60, 1992.

Behrens et al., Science 316: 1185-1188, 2007.

Buchanan-Wollaston et al., J. Cell. Biochem., Supp. 13D, 330, 1989.

Chandler et al., Plant Cell, 1:1175-1183, 1989.
Chandler, In: CRC Handbook of Pest Management in Agriculture, Pimentel (Ed.), I:95-109, 1981.
Comai et al., Nature, 317:741, 1985.
Cork and Khalil, Adv. Appl. Microbiol., 40:289-321, 1995.
Cork and Krueger, Adv. Appl. Microbiol., 36:1-66, 1991.
Coruzzi et al., EMBO J., 3: 1671, 1984.
Creissen et al., Plant J., 8(2):167-175, 1995.
Crop Protection Chemicals Reference, Chemical & Pharmaceutical Press, Inc., NY, 11th Ed., 1803-1821, 1995
De Block et al., EMBO J., 6(9):2513-2518, 1987.
della-Cioppa et al., Proc. Natl. Acad. Sci. USA, 83:6873-6877, 1986.
Ebert et al., Proc. Natl. Acad. Sci. USA, 84:5745-5749, 1987.
European Appln. 553494
European Appln. 646643
Klee et al., Mol. Gen. Genet., 210:437-442, 1987.
Kyte and Doolittle, J. Mol. Biol., 157(1):105-132, 1982.
Lawton et al., Plant Mol. Biol. 9:315-324, 1987.
Mazur, et al., Nucleic Acids Res., 13(7):2373-2386, 1985.
Miki et al., In: Methods in Plant Molecular Biology and Biotechnology, Glick and Thompson (Eds.), CRC Press, 67-88, 1993.
Misawa et al, Plant J., 4:833-840, 1993.
Misawa et al, Plant J., 6:481-489, 1994.
Odell et al., Nature, 313:810-812, 1985.
Padgette et al., Crop Sci., 35:1451-1461, 1995.
PCT Appln. WO 95/06722
PCT Appln. WO 97/41228
PCT Appln. WO 96/38567
PCT Appln. WO 97/31115
PCT Appln. WO 97/11086
PCT Appln. WO 04009761
PCT Appln. WO 04074443
Sathasiivan et al., Nucl. Acids Res., 18:2188-2193, 1990.
Stalker et al., Science, 242:419, 1988.
Stalker et al., Science, 242:419-422, 1988.
Streber and Willmitzer, Bio/Technology, 7:811, 1989.
VanGessel and Majek, 2005 Soybean Weed Management Guide: for Delaware and New Jersey, University of Delaware and Rutgers University, 2005.
Walker et al., Proc. Natl. Acad. Sci. USA, 84:6624, 1987.
Yang and Russell, Proc. Natl. Acad. Sci. USA, 87:4144-4148, 1990.
Zhang et al. Plant Cell, Tissue and Organ Culture 56: 37-46, 1999.

SEQUENCE LISTING

```
<160> NUMBER OF SEQ ID NOS: 32

<210> SEQ ID NO 1
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 1

atggccactt tcgttagaaa cgcttggtac gttgctgcac ttcctgagga gttgagcgag      60

aagcctctag gaagaactat cctcgatact ccactagctc tctatcgtca acctgacgga     120

gttgtcgctg ccctgcttga tatttgtccg catcgcttcg ctccgttgag tgacggtatt     180

ctagtcaacg gacatctcca gtgtccatat cacggtctgg aatttgacgg aggtggccag     240

tgtgtccaca acccgcacgg caacggagcc cgccctgctt ctctgaacgt gcgatcattc     300

cctgtcgtgg aaagagacgc attgatctgg atctgccctg gagatccagc actcgcagat     360

cccggtgcta tccctgactt tgggtgtcgt gttgatccag cttaccgtac tgtcggaggt     420

tacggtcacg tggactgcaa ctacaagctc cttgtggata acctcatgga tcttggacac     480

gctcagtacg tgcaccgcgc taacgcccaa acagacgcct tcgatagact tgagcgtgag     540

gtgatcgttg gcgacggcga gatccaggcg ctcatgaaga tccctggtgg cacaccctca     600

gttctcatgg ctaagttctt gcgtggtgct aacacaccag ttgacgcctg gaacgacatc     660

cggtggaata aggtgtcggc tatgctgaac ttcatcgcgg tcgcgccgga agggacgccg     720

aaggagcagt caatccactc ccgaggaacc catatcctta ctcctgagac cgaggcaagc     780

tgccattact tcttcggtag ttcccgcaac ttcggtatag acgatccaga gatggacggt     840

gttctcagga gctggcaagc tcaagccctg gtgaaggagg acaaagtggt cgttgaagct     900

atcgaaaggc ggagggctta cgtcgaagcg aacgggatca gacccgccat gttgtcctgc     960

gacgaggcag ccgtcagggt atccagggag attgagaagc tcgaacaact agaagcggcg    1020

tga                                                                  1023
```

<210> SEQ ID NO 2
<211> LENGTH: 340
<212> TYPE: PRT
<213> ORGANISM: Artificial
<220> FEATURE:
<223> OTHER INFORMATION: Based on dicamba monooxygenase gene from
Pseudomonas maltophilia

<400> SEQUENCE: 2

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340
```

<210> SEQ ID NO 3

<211> LENGTH: 1023
<212> TYPE: DNA
<213> ORGANISM: Artificial
<220> FEATURE:
<223> OTHER INFORMATION: Based on dicamba monooxygenase gene from
Pseudomonas maltophilia

<400> SEQUENCE: 3 atgctcactt tcgttagaaa cgcttggtac gttgctgcac ttcctgagga gttgagcgag 60 aagcctctag gaagaactat cctcgatact ccactagctc tctatcgtca acctgacgga 120 gttgtcgctg ccctgcttga tatttgtccg catcgcttcg ctccgttgag tgacggtatt 180 ctagtcaacg gacatctcca gtgtccatat cacggtctgg aatttgacgg aggtggccag 240 tgtgtccaca acccgcacgg caacggagcc cgccctgctt ctctgaacgt gcgatcattc 300 cctgtcgtgg aaagagacgc attgatctgg atctgccctg gagatccagc actcgcagat 360 cccggtgcta tccctgactt tgggtgtcgt gttgatccag cttaccgtac tgtcggaggt 420 tacggtcacg tggactgcaa ctacaagctc cttgtggata acctcatgga tcttggacac 480 gctcagtacg tgcaccgcgc taacgcccaa acagacgcct tcgatagact tgagcgtgag 540 gtgatcgttg gcgacggcga gatccaggcg ctcatgaaga tccctggtgg cacaccctca 600 gttctcatgg ctaagttctt gcgtggtgct aacacaccag ttgacgcctg gaacgacatc 660 cggtggaata aggtgtcggc tatgctgaac ttcatcgcgg tcgcgccgga agggacgccg 720 aaggagcagt caatccactc ccgaggaacc catatcctta ctcctgagac cgaggcaagc 780 tgccattact tcttcggtag ttcccgcaac ttcggtatag acgatccaga gatggacggt 840 gttctcagga gctggcaagc tcaagccctg gtgaaggagg acaaagtggt cgttgaagct 900 atcgaaaggc ggagggctta cgtcgaagcg aacgggatca gacccgccat gttgtcctgc 960 gacgaggcag ccgtcagggt atccagggag attgagaagc tcgaacaact agaagcggcg 1020 tga 1023

<210> SEQ ID NO 4
<211> LENGTH: 340
<212> TYPE: PRT
<213> ORGANISM: Artificial
<220> FEATURE:
<223> OTHER INFORMATION: Based on dicamba monooxygenase gene from
Pseudomonas maltophilia

<400> SEQUENCE: 4

Met Leu Thr Phe Val Arg Asn Ala Trp Tyr Val Ala Ala Leu Pro Glu
1 5 10 15

Glu Leu Ser Glu Lys Pro Leu Gly Arg Thr Ile Leu Asp Thr Pro Leu
20 25 30

Ala Leu Tyr Arg Gln Pro Asp Gly Val Val Ala Ala Leu Leu Asp Ile
35 40 45

Cys Pro His Arg Phe Ala Pro Leu Ser Asp Gly Ile Leu Val Asn Gly
50 55 60

His Leu Gln Cys Pro Tyr His Gly Leu Glu Phe Asp Gly Gly Gly Gln
65 70 75 80

Cys Val His Asn Pro His Gly Asn Gly Ala Arg Pro Ala Ser Leu Asn
85 90 95

Val Arg Ser Phe Pro Val Val Glu Arg Asp Ala Leu Ile Trp Ile Cys
100 105 110

Pro Gly Asp Pro Ala Leu Ala Asp Pro Gly Ala Ile Pro Asp Phe Gly
115 120 125

```
Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340


<210> SEQ ID NO 5
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 5

atgctcactt tcgttagaaa cgcttggtac gttgctgcac ttcctgagga gttgagcgag     60

aagcctctag gaagaactat cctcgatact ccactagctc tctatcgtca acctgacgga    120

gttgtcgctg ccctgcttga tatttgtccg catcgcttcg ctccgttgag tgacggtatt    180

ctagtcaacg gacatctcca gtgtccatat cacggtctgg aatttgacgg aggtggccag    240

tgtgtccaca acccgcacgg caacggagcc cgccctgctt ctctgaacgt gcgatcattc    300

cctgtcgtgg aaagagacgc attgatctgg atctggcctg gagatccagc actcgcagat    360

cccggtgcta tccctgactt tgggtgtcgt gttgatccag cttaccgtac tgtcggaggt    420

tacggtcacg tggactgcaa ctacaagctc cttgtggata acctcatgga tcttggacac    480

gctcagtacg tgcaccgcgc taacgcccaa acagacgcct tcgatagact tgagcgtgag    540

gtgatcgttg gcgacggcga gatccaggcg ctcatgaaga tccctggtgg cacaccctca    600

gttctcatgg ctaagttctt gcgtggtgct aacacaccag ttgacgcctg gaacgacatc    660

cggtggaata aggtgtcggc tatgctgaac ttcatcgcgg tcgcgccgga agggacgccg    720

aaggagcagt caatccactc ccgaggaacc catatcctta ctcctgagac cgaggcaagc    780
```

```
tgccattact tcttcggtag ttcccgcaac ttcggtatag acgatccaga gatggacggt    840

gttctcagga gctggcaagc tcaagccctg gtgaaggagg acaaagtggt cgttgaagct    900

atcgaaaggc ggagggctta cgtcgaagcg aacgggatca gacccgccat gttgtcctgc    960

gacgaggcag ccgtcagggt atccagggag attgagaagc tcgaacaact agaagcggcg   1020

tga                                                                 1023


<210> SEQ ID NO 6
<211> LENGTH: 340
<212> TYPE: PRT
<213> ORGANISM: Artificial
<220> FEATURE:
<223> OTHER INFORMATION: Based on dicamba monooxygenase gene from
      Pseudomonas maltophilia

<400> SEQUENCE: 6

Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Glu Ala Ile Glu Arg Arg
    290                 295                 300
```

```
Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340


<210> SEQ ID NO 7
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 7

atggccacct tcgtccgcaa tgcctggtat gtggcggcgc tgcccgagga actgtccgaa     60

aagccgctcg gccggacgat tctcgacaca ccgctcgcgc tctaccgcca gcccgacggt    120

gtggtcgcgg cgctgctcga catctgtccg caccgcttcg cgccgctgag cgacggcatc    180

ctcgtcaacg gccatctcca atgcccctat cacgggctgg aattcgatgg cggcgggcag    240

tgcgtccata acccgcacgg caatggcgcc cgcccggctt cgctcaacgt ccgctccttc    300

ccggtggtgg agcgcgacgc gctgatctgg atctgtcccg gcgatccggc gctggccgat    360

cctggggcga tccccgactt cggctgccgc gtcgatcccg cctatcggac cgtcggcggc    420

tatgggcatg tcgactgcaa ctacaagctg ctggtcgaca acctgatgga cctcggccac    480

gcccaatatg tccatcgcgc caacgcccag accgacgcct tcgaccggct ggagcgcgag    540

gtgatcgtcg gcgacggtga gatacaggcg ctgatgaaga ttcccggcgg cacgccgagc    600

gtgctgatgg ccaagttcct gcgcggcgcc aatacccccg tcgacgcttg gaacgacatc    660

cgctggaaca aggtgagcgc gatgctcaac ttcatcgcgg tggcgccgga aggcaccccg    720

aaggagcaga gcatccactc gcgcggtacc catatcctga cccccgagac ggaggcgagc    780

tgccattatt tcttcggctc ctcgcgcaat ttcggcatcg acgatccgga gatggacggc    840

gtgctgcgca gctggcaggc tcaggcgctg gtcaaggagg acaaggtcgt cgtcgaggcg    900

atcgagcgcc gccgcgccta tgtcgaggcg aatggcatcc gcccggcgat gctgtcgtgc    960

gacgaagccg cagtccgtgt cagccgcgag atcgagaagc ttgagcagct cgaagccgcc   1020

tga                                                                 1023


<210> SEQ ID NO 8
<211> LENGTH: 340
<212> TYPE: PRT
<213> ORGANISM: Artificial
<220> FEATURE:
<223> OTHER INFORMATION: Based on dicamba monooxygenase gene from
      Pseudomonas maltophilia

<400> SEQUENCE: 8

Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60
```

```
His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340


<210> SEQ ID NO 9
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 9

atggccactt tcgttagaaa cgcttggtac gttgctgcac ttcctgagga gttgagcgag      60

aagcctctag gaagaactat cctcgatact ccactagctc tctatcgtca acctgacgga     120

gttgtcgctg ccctgcttga tatttgtccg catcgcttcg ctccgttgag tgacggtatt     180

ctagtcaacg gacatctcca gtgtccatat cacggtctgg aatttgacgg aggtggccag     240

tgtgtccaca acccgcacgg caacggagcc cgccctgctt ctctgaacgt gcgatcattc     300

cctgtcgtgg aaagagacgc attgatctgg atctggcctg gagatccagc actcgcagat     360

cccggtgcta tccctgactt tgggtgtcgt gttgatccag cttaccgtac tgtcggaggt     420
```

```
tacggtcacg tggactgcaa ctacaagctc cttgtggata acctcatgga tcttggacac    480

gctcagtacg tgcaccgcgc taacgcccaa acagacgcct tcgatagact tgagcgtgag    540

gtgatcgttg gcgacggcga gatccaggcg ctcatgaaga tccctggtgg cacaccctca    600

gttctcatgg ctaagttctt gcgtggtgct aacacaccag ttgacgcctg gaacgacatc    660

cggtggaata aggtgtcggc tatgctgaac ttcatcgcgg tcgcgccgga agggacgccg    720

aaggagcagt caatccactc ccgaggaacc catatcctta ctcctgagac cgaggcaagc    780

tgccattact tcttcggtag ttcccgcaac ttcggtatag acgatccaga gatggacggt    840

gttctcagga gctggcaagc tcaagccctg gtgaaggagg acaaagtggt cgttgaagct    900

atcgaaaggc ggagggctta cgtcgaagcg aacgggatca gacccgccat gttgtcctgc    960

gacgaggcag ccgtcagggt atccagggag attgagaagc tcgaacaact agaagcggcg   1020

tga                                                                 1023


<210> SEQ ID NO 10
<211> LENGTH: 340
<212> TYPE: PRT
<213> ORGANISM: Artificial
<220> FEATURE:
<223> OTHER INFORMATION: Based on dicamba monooxygenase gene from
      Pseudomonas maltophilia

<400> SEQUENCE: 10

Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
```

```
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340


<210> SEQ ID NO 11
<211> LENGTH: 1020
<212> TYPE: DNA
<213> ORGANISM: Pseudomonas maltophilia

<400> SEQUENCE: 11

atgaccttcg tccgcaatgc ctggtatgtg gcggcgctgc ccgaggaact gtccgaaaag     60

ccgctcggcc ggacgattct cgacacaccg ctcgcgctct accgccagcc cgacggtgtg    120

gtcgcggcgc tgctcgacat ctgtccgcac cgcttcgcgc cgctgagcga cggcatcctc    180

gtcaacggcc atctccaatg cccctatcac gggctggaat tcgatggcgg cgggcagtgc    240

gtccataacc cgcacggcaa tggcgcccgc ccggcttcgc tcaacgtccg ctccttcccg    300

gtggtggagc gcgacgcgct gatctggatc tggcccggcg atccggcgct ggccgatcct    360

ggggcgatcc ccgacttcgg ctgccgcgtc gatcccgcct atcggaccgt cggcggctat    420

gggcatgtcg actgcaacta caagctgctg gtcgacaacc tgatggacct cggccacgcc    480

caatatgtcc atcgcgccaa cgcccagacc gacgccttcg accggctgga gcgcgaggtg    540

atcgtcggcg acggtgagat acaggcgctg atgaagattc ccggcggcac gccgagcgtg    600

ctgatggcca agttcctgcg cggcgccaat acccccgtcg acgcttggaa cgacatccgc    660

tggaacaagg tgagcgcgat gctcaacttc atcgcggtgg cgccggaagg caccccgaag    720

gagcagagca tccactcgcg cggtacccat atcctgaccc ccgagacgga ggcgagctgc    780

cattatttct tcggctcctc gcgcaatttc ggcatcgacg atccggagat ggacggcgtg    840

ctgcgcagct ggcaggctca ggcgctggtc aaggaggaca aggtcgtcgt cgaggcgatc    900

gagcgccgcc gcgcctatgt cgaggcgaat ggcatccgcc cggcgatgct gtcgtgcgac    960

gaagccgcag tccgtgtcag ccgcgagatc gagaagcttg agcagctcga agccgcctga   1020


<210> SEQ ID NO 12
<211> LENGTH: 339
<212> TYPE: PRT
<213> ORGANISM: Pseudomonas maltophilia

<400> SEQUENCE: 12

Met Thr Phe Val Arg Asn Ala Trp Tyr Val Ala Ala Leu Pro Glu Glu
1               5                   10                  15

Leu Ser Glu Lys Pro Leu Gly Arg Thr Ile Leu Asp Thr Pro Leu Ala
            20                  25                  30

Leu Tyr Arg Gln Pro Asp Gly Val Val Ala Ala Leu Leu Asp Ile Cys
        35                  40                  45
```

```
Pro His Arg Phe Ala Pro Leu Ser Asp Gly Ile Leu Val Asn Gly His
    50                  55                  60

Leu Gln Cys Pro Tyr His Gly Leu Glu Phe Asp Gly Gly Gly Gln Cys
65                  70                  75                  80

Val His Asn Pro His Gly Asn Gly Ala Arg Pro Ala Ser Leu Asn Val
                85                  90                  95

Arg Ser Phe Pro Val Val Glu Arg Asp Ala Leu Ile Trp Ile Trp Pro
            100                 105                 110

Gly Asp Pro Ala Leu Ala Asp Pro Gly Ala Ile Pro Asp Phe Gly Cys
        115                 120                 125

Arg Val Asp Pro Ala Tyr Arg Thr Val Gly Gly Tyr Gly His Val Asp
    130                 135                 140

Cys Asn Tyr Lys Leu Leu Val Asp Asn Leu Met Asp Leu Gly His Ala
145                 150                 155                 160

Gln Tyr Val His Arg Ala Asn Ala Gln Thr Asp Ala Phe Asp Arg Leu
                165                 170                 175

Glu Arg Glu Val Ile Val Gly Asp Gly Glu Ile Gln Ala Leu Met Lys
            180                 185                 190

Ile Pro Gly Gly Thr Pro Ser Val Leu Met Ala Lys Phe Leu Arg Gly
        195                 200                 205

Ala Asn Thr Pro Val Asp Ala Trp Asn Asp Ile Arg Trp Asn Lys Val
    210                 215                 220

Ser Ala Met Leu Asn Phe Ile Ala Val Ala Pro Glu Gly Thr Pro Lys
225                 230                 235                 240

Glu Gln Ser Ile His Ser Arg Gly Thr His Ile Leu Thr Pro Glu Thr
                245                 250                 255

Glu Ala Ser Cys His Tyr Phe Phe Gly Ser Ser Arg Asn Phe Gly Ile
            260                 265                 270

Asp Asp Pro Glu Met Asp Gly Val Leu Arg Ser Trp Gln Ala Gln Ala
        275                 280                 285

Leu Val Lys Glu Asp Lys Val Val Val Glu Ala Ile Glu Arg Arg Arg
    290                 295                 300

Ala Tyr Val Glu Ala Asn Gly Ile Arg Pro Ala Met Leu Ser Cys Asp
305                 310                 315                 320

Glu Ala Ala Val Arg Val Ser Arg Glu Ile Glu Lys Leu Glu Gln Leu
                325                 330                 335

Glu Ala Ala


<210> SEQ ID NO 13
<211> LENGTH: 455
<212> TYPE: PRT
<213> ORGANISM: Agrobacterium tumefaciens

<400> SEQUENCE: 13

Met Leu His Gly Ala Ser Ser Arg Pro Ala Thr Ala Arg Lys Ser Ser
1               5                   10                  15

Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80
```

```
Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Asp Ala Thr Met Ile Ala Thr Ser
            420                 425                 430

Phe Pro Glu Phe Met Asp Leu Met Ala Gly Leu Gly Ala Lys Ile Glu
        435                 440                 445

Leu Ser Asp Thr Lys Ala Ala
    450                 455


<210> SEQ ID NO 14
<211> LENGTH: 448
<212> TYPE: PRT
<213> ORGANISM: Artificial
<220> FEATURE:
<223> OTHER INFORMATION: Variant TIPA EPSPS derived from lettuce
```

<400> SEQUENCE: 14

Lys Pro Ser Thr Ala Pro Glu Glu Ile Val Leu Gln Pro Ile Lys Glu
1 5 10 15

Ile Ser Gly Thr Val Asn Leu Pro Gly Ser Lys Ser Leu Ser Asn Arg
20 25 30

Ile Leu Leu Leu Ala Ala Leu Ser Glu Gly Thr Thr Val Val Asp Asn
35 40 45

Leu Leu Asn Ser Asp Asp Val His Tyr Met Leu Gly Ala Leu Arg Ala
50 55 60

Leu Gly Leu His Val Glu Glu Asn Gly Ala Leu Lys Arg Ala Ile Val
65 70 75 80

Glu Gly Cys Gly Gly Val Phe Pro Val Gly Arg Glu Ser Lys Asp Glu
85 90 95

Ile Gln Leu Phe Leu Gly Asn Ala Gly Ile Ala Met Arg Ala Leu Thr
100 105 110

Ala Ala Val Thr Ala Ala Gly Gly Ser Ser Ser Tyr Ile Leu Asp Gly
115 120 125

Val Pro Arg Met Arg Glu Arg Pro Ile Gly Asp Leu Val Thr Gly Leu
130 135 140

Lys Gln Leu Gly Ala Asp Val Asp Cys Phe Leu Gly Thr Asp Cys Pro
145 150 155 160

Pro Val Arg Val Val Gly Ser Gly Gly Leu Pro Gly Gly Lys Val Lys
165 170 175

Leu Ser Gly Ser Ile Ser Ser Gln Tyr Leu Thr Ala Leu Leu Met Ala
180 185 190

Ala Pro Leu Ala Leu Gly Asp Val Glu Ile Glu Ile Ile Asp Lys Leu
195 200 205

Ile Ser Ile Pro Tyr Val Glu Met Thr Leu Lys Leu Met Glu Arg Phe
210 215 220

Gly Val Ser Val Gln His Ser Asp Thr Trp Asp Arg Phe His Val Gln
225 230 235 240

Gly Gly Gln Lys Tyr Lys Ser Pro Gly Asn Ala Tyr Val Glu Gly Asp
245 250 255

Ala Ser Ser Ala Ser Tyr Phe Leu Ala Gly Ala Ala Ile Thr Gly Gly
260 265 270

Thr Ile Thr Val Glu Gly Cys Gly Thr Ser Ser Leu Gln Gly Asp Val
275 280 285

Lys Phe Ala Glu Val Leu Gly Gln Met Gly Ala Gln Val Thr Trp Thr
290 295 300

Glu Asn Ser Val Thr Val Lys Gly Pro Pro Arg Asp Pro Ser Gly Arg
305 310 315 320

Lys His Leu Arg Pro Val Asp Val Asn Met Asn Lys Met Pro Asp Val
325 330 335

Ala Met Thr Leu Ala Val Val Ala Leu Tyr Ala Asp Gly Pro Thr Ala
340 345 350

Ile Arg Asp Val Ala Ser Trp Arg Val Lys Glu Thr Glu Arg Met Ile
355 360 365

Ala Ile Cys Thr Glu Leu Arg Lys Leu Gly Ala Thr Val Glu Glu Gly
370 375 380

Pro Asp Tyr Cys Ile Ile Thr Pro Pro Glu Lys Leu Asn Val Thr Ala
385 390 395 400

```
Ile Asp Thr Tyr Asp Asp His Arg Met Ala Met Ala Phe Ser Leu Ala
                405                 410                 415

Ala Cys Ala Asp Val Ala Val Thr Ile Lys Asp Pro Gly Cys Thr Arg
            420                 425                 430

Lys Thr Phe Pro Asp Tyr Phe Glu Val Leu Gln Arg Phe Ala Lys His
        435                 440                 445


<210> SEQ ID NO 15
<211> LENGTH: 434
<212> TYPE: PRT
<213> ORGANISM: Artificial
<220> FEATURE:
<223> OTHER INFORMATION: Variant TIPA EPSPS derived from Zea mays

<400> SEQUENCE: 15

Ile Lys Glu Ile Ser Gly Thr Val Lys Leu Pro Gly Ser Lys Ser Leu
1               5                   10                  15

Ser Asn Arg Ile Leu Leu Leu Ala Ala Leu Ser Glu Gly Thr Thr Val
            20                  25                  30

Val Asp Asn Leu Leu Asn Ser Glu Asp Val His Tyr Met Leu Gly Ala
        35                  40                  45

Leu Arg Thr Leu Gly Leu Ser Val Glu Ala Asp Lys Ala Ala Lys Arg
    50                  55                  60

Ala Val Val Val Gly Cys Gly Gly Lys Phe Pro Val Glu Asp Ala Lys
65                  70                  75                  80

Glu Glu Val Gln Leu Phe Leu Gly Asn Ala Gly Ile Ala Met Arg Ala
                85                  90                  95

Leu Thr Ala Ala Val Thr Ala Ala Gly Gly Asn Ala Thr Tyr Val Leu
            100                 105                 110

Asp Gly Val Pro Arg Met Arg Glu Arg Pro Ile Gly Asp Leu Val Val
        115                 120                 125

Gly Leu Lys Gln Leu Gly Ala Asp Val Asp Cys Phe Leu Gly Thr Asp
    130                 135                 140

Cys Pro Pro Val Arg Val Asn Gly Ile Gly Gly Leu Pro Gly Gly Lys
145                 150                 155                 160

Val Lys Leu Ser Gly Ser Ile Ser Ser Gln Tyr Leu Ser Ala Leu Leu
                165                 170                 175

Met Ala Ala Pro Leu Ala Leu Gly Asp Val Glu Ile Glu Ile Ile Asp
            180                 185                 190

Lys Leu Ile Ser Ile Pro Tyr Val Glu Met Thr Leu Arg Leu Met Glu
        195                 200                 205

Arg Phe Gly Val Lys Ala Glu His Ser Asp Ser Trp Asp Arg Phe Tyr
    210                 215                 220

Ile Lys Gly Gly Gln Lys Tyr Lys Ser Pro Lys Asn Ala Tyr Val Glu
225                 230                 235                 240

Gly Asp Ala Ser Ser Ala Ser Tyr Phe Leu Ala Gly Ala Ala Ile Thr
                245                 250                 255

Gly Gly Thr Val Thr Val Glu Gly Cys Gly Thr Thr Ser Leu Gln Gly
            260                 265                 270

Asp Val Lys Phe Ala Glu Val Leu Glu Met Met Gly Ala Lys Val Thr
        275                 280                 285

Trp Thr Glu Thr Ser Val Thr Val Thr Gly Pro Pro Arg Glu Pro Phe
    290                 295                 300

Gly Arg Lys His Leu Lys Ala Ile Asp Val Asn Met Asn Lys Met Pro
305                 310                 315                 320
```

```
Asp Val Ala Met Thr Leu Ala Val Val Ala Leu Phe Ala Asp Gly Pro
                325                 330                 335

Thr Ala Ile Arg Asp Val Ala Ser Trp Arg Val Lys Glu Thr Glu Arg
            340                 345                 350

Met Val Ala Ile Arg Thr Glu Leu Thr Lys Leu Gly Ala Ser Val Glu
        355                 360                 365

Glu Gly Pro Asp Tyr Cys Ile Ile Thr Pro Pro Glu Lys Leu Asn Val
    370                 375                 380

Thr Ala Ile Asp Thr Tyr Asp Asp His Arg Met Ala Met Ala Phe Ser
385                 390                 395                 400

Leu Ala Ala Cys Ala Glu Val Pro Val Thr Ile Arg Asp Pro Gly Cys
                405                 410                 415

Thr Arg Lys Thr Phe Pro Asp Tyr Phe Asp Val Leu Ser Thr Phe Val
            420                 425                 430

Lys Asn


<210> SEQ ID NO 16
<211> LENGTH: 428
<212> TYPE: PRT
<213> ORGANISM: Xanthomonas campestris

<400> SEQUENCE: 16

Met Lys Ile Tyr Lys Leu Gln Thr Pro Val Asn Ala Ile Leu Glu Asn
1               5                   10                  15

Ile Ala Ala Asp Lys Ser Ile Ser His Arg Phe Ala Ile Phe Ser Leu
            20                  25                  30

Leu Thr Gln Glu Glu Asn Lys Ala Gln Asn Tyr Leu Leu Ala Gln Asp
        35                  40                  45

Thr Leu Asn Thr Leu Glu Ile Ile Lys Asn Leu Gly Ala Lys Ile Glu
    50                  55                  60

Gln Lys Asp Ser Cys Val Lys Ile Ile Pro Pro Lys Glu Ile Leu Ser
65                  70                  75                  80

Pro Asn Cys Ile Leu Asp Cys Gly Asn Ser Gly Thr Ala Met Arg Leu
                85                  90                  95

Met Ile Gly Phe Leu Ala Gly Ile Ser Gly Phe Phe Val Leu Ser Gly
            100                 105                 110

Asp Lys Tyr Leu Asn Asn Arg Pro Met Arg Arg Ile Ser Lys Pro Leu
        115                 120                 125

Thr Gln Ile Gly Ala Arg Ile Tyr Gly Arg Asn Glu Ala Asn Leu Ala
    130                 135                 140

Pro Leu Cys Ile Glu Gly Gln Lys Leu Lys Ala Phe Asn Phe Lys Ser
145                 150                 155                 160

Glu Ile Ser Ser Ala Gln Val Lys Thr Ala Met Ile Leu Ser Ala Phe
                165                 170                 175

Arg Ala Asp Asn Val Cys Thr Phe Ser Glu Ile Ser Leu Ser Arg Asn
            180                 185                 190

His Ser Glu Asn Met Leu Lys Ala Met Lys Ala Pro Ile Arg Val Ser
        195                 200                 205

Asn Asp Gly Leu Ser Leu Glu Ile Asn Pro Leu Lys Lys Pro Leu Lys
    210                 215                 220

Ala Gln Asn Ile Ile Ile Pro Asn Asp Pro Ser Ser Ala Phe Tyr Phe
225                 230                 235                 240

Val Leu Ala Ala Ile Ile Leu Pro Lys Ser Gln Ile Ile Leu Lys Asn
                245                 250                 255
```

```
Ile Leu Leu Asn Pro Thr Arg Ile Glu Ala Tyr Lys Ile Leu Gln Lys
            260                 265                 270

Met Gly Ala Lys Leu Glu Met Thr Ile Thr Gln Asn Asp Phe Glu Thr
        275                 280                 285

Ile Gly Glu Ile Arg Val Glu Ser Ser Lys Leu Asn Gly Ile Glu Val
    290                 295                 300

Lys Asp Asn Ile Ala Trp Leu Ile Asp Glu Ala Pro Ala Leu Ala Ile
305                 310                 315                 320

Ala Phe Ala Leu Ala Lys Gly Lys Ser Ser Leu Ile Asn Ala Lys Glu
                325                 330                 335

Leu Arg Val Lys Glu Ser Asp Arg Ile Ala Val Met Val Glu Asn Leu
            340                 345                 350

Lys Leu Cys Gly Val Glu Ala Arg Glu Leu Asp Asp Gly Phe Glu Ile
        355                 360                 365

Glu Gly Gly Cys Glu Leu Lys Ser Ser Lys Ile Lys Ser Tyr Gly Asp
    370                 375                 380

His Arg Ile Ala Met Ser Phe Ala Ile Leu Gly Leu Leu Cys Gly Ile
385                 390                 395                 400

Glu Ile Asp Asp Ser Asp Cys Ile Lys Thr Ser Phe Pro Asn Phe Ile
                405                 410                 415

Glu Ile Leu Ser Asn Leu Gly Ala Arg Ile Asp Tyr
            420                 425


<210> SEQ ID NO 17
<211> LENGTH: 443
<212> TYPE: PRT
<213> ORGANISM: Caulobacter crescentus

<400> SEQUENCE: 17

Met Ser Leu Ala Gly Leu Lys Ser Ala Pro Gly Gly Ala Leu Arg Gly
1               5                   10                  15

Ile Val Arg Ala Pro Gly Asp Lys Ser Ile Ser His Arg Ser Met Ile
            20                  25                  30

Leu Gly Ala Leu Ala Thr Gly Thr Thr Thr Val Glu Gly Leu Leu Glu
        35                  40                  45

Gly Asp Asp Val Leu Ala Thr Ala Arg Ala Met Gln Ala Phe Gly Ala
    50                  55                  60

Arg Ile Glu Arg Glu Gly Val Gly Arg Trp Arg Ile Glu Gly Lys Gly
65                  70                  75                  80

Gly Phe Glu Glu Pro Val Asp Val Ile Asp Cys Gly Asn Ala Gly Thr
                85                  90                  95

Gly Val Arg Leu Ile Met Gly Ala Ala Ala Gly Phe Ala Met Cys Ala
            100                 105                 110

Thr Phe Thr Gly Asp Gln Ser Leu Arg Gly Arg Pro Met Gly Arg Val
        115                 120                 125

Leu Asp Pro Leu Ala Arg Met Gly Ala Thr Trp Leu Gly Arg Asp Lys
    130                 135                 140

Gly Arg Leu Pro Leu Thr Leu Lys Gly Gly Asn Leu Arg Gly Leu Asn
145                 150                 155                 160

Tyr Thr Leu Pro Met Ala Ser Ala Gln Val Lys Ser Ala Val Leu Leu
                165                 170                 175

Ala Gly Leu His Ala Glu Gly Gly Val Glu Val Ile Glu Pro Glu Ala
            180                 185                 190

Thr Arg Asp His Thr Glu Arg Met Leu Arg Ala Phe Gly Ala Glu Val
```

```
        195                 200                 205

Ile Val Glu Asp Arg Lys Ala Gly Asp Lys Thr Phe Arg His Val Arg
    210                 215                 220

Leu Pro Glu Gly Gln Lys Leu Thr Gly Thr His Val Ala Val Pro Gly
225                 230                 235                 240

Asp Pro Ser Ser Ala Ala Phe Pro Leu Val Ala Ala Leu Ile Val Pro
                245                 250                 255

Gly Ser Glu Val Thr Val Glu Gly Val Met Leu Asn Glu Leu Arg Thr
            260                 265                 270

Gly Leu Phe Thr Thr Leu Gln Glu Met Gly Ala Asp Leu Val Ile Ser
        275                 280                 285

Asn Val Arg Val Ala Ser Gly Glu Glu Val Gly Asp Ile Thr Ala Arg
    290                 295                 300

Tyr Ser Gln Leu Lys Gly Val Val Val Pro Pro Glu Arg Ala Pro Ser
305                 310                 315                 320

Met Ile Asp Glu Tyr Pro Ile Leu Ala Val Ala Ala Ala Phe Ala Ser
                325                 330                 335

Gly Glu Thr Val Met Arg Gly Val Gly Glu Met Arg Val Lys Glu Ser
            340                 345                 350

Asp Arg Ile Ser Leu Thr Ala Asn Gly Leu Lys Ala Cys Gly Val Gln
        355                 360                 365

Val Val Glu Glu Pro Glu Gly Phe Ile Val Thr Gly Thr Gly Gln Pro
    370                 375                 380

Pro Lys Gly Gly Ala Thr Val Val Thr His Gly Asp His Arg Ile Ala
385                 390                 395                 400

Met Ser His Leu Ile Leu Gly Met Ala Ala Gln Ala Glu Val Ala Val
                405                 410                 415

Asp Glu Pro Gly Met Ile Ala Thr Ser Phe Pro Gly Phe Ala Asp Leu
            420                 425                 430

Met Arg Gly Leu Gly Ala Thr Leu Ala Glu Ala
        435                 440


<210> SEQ ID NO 18
<211> LENGTH: 441
<212> TYPE: DNA
<213> ORGANISM: Artificial
<220> FEATURE:
<223> OTHER INFORMATION: Artificial primer
<220> FEATURE:
<221> NAME/KEY: CDS
<222> LOCATION: (1)..(441)

<400> SEQUENCE: 18

atg ata gag gtg aaa ccg att aac gca gag gat acc tat gaa cta agg       48
Met Ile Glu Val Lys Pro Ile Asn Ala Glu Asp Thr Tyr Glu Leu Arg
1               5                   10                  15

cat aga ata ctc aga cca aac cag ccg ata gaa gcg tgt atg ttt gaa       96
His Arg Ile Leu Arg Pro Asn Gln Pro Ile Glu Ala Cys Met Phe Glu
            20                  25                  30

agc gat tta ctt cgt ggt gca ttt cac tta ggc ggc ttt tac agg ggc      144
Ser Asp Leu Leu Arg Gly Ala Phe His Leu Gly Gly Phe Tyr Arg Gly
        35                  40                  45

aaa ctg att tcc ata gct tca ttc cac cag gcc gag cac tcg gaa ctc      192
Lys Leu Ile Ser Ile Ala Ser Phe His Gln Ala Glu His Ser Glu Leu
    50                  55                  60

caa ggc cag aaa cag tac cag ctc cga ggt atg gct acc ttg gaa ggt      240
Gln Gly Gln Lys Gln Tyr Gln Leu Arg Gly Met Ala Thr Leu Glu Gly
65                  70                  75                  80
```

```
tat cgt gag cag aaa gcg gga tca act cta gtt aaa cac gct gaa gaa      288
Tyr Arg Glu Gln Lys Ala Gly Ser Thr Leu Val Lys His Ala Glu Glu
                85                  90                  95

atc ctt cgt aag agg ggg gcg gac atg ctt tgg tgt aat gcg agg aca      336
Ile Leu Arg Lys Arg Gly Ala Asp Met Leu Trp Cys Asn Ala Arg Thr
            100                 105                 110

tcc gcc tca ggc tac tac aaa aag tta ggc ttc agc gag cag gga gag      384
Ser Ala Ser Gly Tyr Tyr Lys Lys Leu Gly Phe Ser Glu Gln Gly Glu
        115                 120                 125

ata ttt gac acg ccg cca gta gga cct cac atc ctg atg tat aaa agg      432
Ile Phe Asp Thr Pro Pro Val Gly Pro His Ile Leu Met Tyr Lys Arg
    130                 135                 140

atc aca taa                                                          441
Ile Thr
145


<210> SEQ ID NO 19
<211> LENGTH: 146
<212> TYPE: PRT
<213> ORGANISM: Artificial
<220> FEATURE:
<223> OTHER INFORMATION: Synthetic Construct

<400> SEQUENCE: 19

Met Ile Glu Val Lys Pro Ile Asn Ala Glu Asp Thr Tyr Glu Leu Arg
1               5                   10                  15

His Arg Ile Leu Arg Pro Asn Gln Pro Ile Glu Ala Cys Met Phe Glu
            20                  25                  30

Ser Asp Leu Leu Arg Gly Ala Phe His Leu Gly Gly Phe Tyr Arg Gly
        35                  40                  45

Lys Leu Ile Ser Ile Ala Ser Phe His Gln Ala Glu His Ser Glu Leu
    50                  55                  60

Gln Gly Gln Lys Gln Tyr Gln Leu Arg Gly Met Ala Thr Leu Glu Gly
65                  70                  75                  80

Tyr Arg Glu Gln Lys Ala Gly Ser Thr Leu Val Lys His Ala Glu Glu
                85                  90                  95

Ile Leu Arg Lys Arg Gly Ala Asp Met Leu Trp Cys Asn Ala Arg Thr
            100                 105                 110

Ser Ala Ser Gly Tyr Tyr Lys Lys Leu Gly Phe Ser Glu Gln Gly Glu
        115                 120                 125

Ile Phe Asp Thr Pro Pro Val Gly Pro His Ile Leu Met Tyr Lys Arg
    130                 135                 140

Ile Thr
145


<210> SEQ ID NO 20
<211> LENGTH: 433
<212> TYPE: DNA
<213> ORGANISM: Artificial Sequence
<220> FEATURE:
<223> OTHER INFORMATION: Based on PClSV promoter sequence

<400> SEQUENCE: 20

agatcttgag ccaatcaaag aggagtgatg tagacctaaa gcaataatgg agccatgacg     60

taagggctta cgcccatacg aaataattaa aggctgatgt gacctgtcgg tctctcagaa    120

cctttacttt ttatgtttgg cgtgtatttt taaatttcca cggcaatgac gatgtgaccc    180

aacgagatct tgagccaatc aaagaggagt gatgtagacc taaagcaata atggagccat    240
```

```
gacgtaaggg cttacgccca tacgaaataa ttaaaggctg atgtgacctg tcggtctctc    300

agaaccttta ctttttatat ttggcgtgta tttttaaatt tccacggcaa tgacgatgtg    360

acctgtgcat ccgctttgcc tataaataag ttttagtttg tattgatcga cacggtcgag    420

aagacacggc cat                                                       433


<210> SEQ ID NO 21
<211> LENGTH: 57
<212> TYPE: PRT
<213> ORGANISM: Pisum sativum

<400> SEQUENCE: 21

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys
    50                  55


<210> SEQ ID NO 22
<211> LENGTH: 85
<212> TYPE: PRT
<213> ORGANISM: Arabidopsis thaliana

<400> SEQUENCE: 22

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85


<210> SEQ ID NO 23
<211> LENGTH: 76
<212> TYPE: PRT
<213> ORGANISM: Arabidopsis thaliana

<400> SEQUENCE: 23

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75


<210> SEQ ID NO 24
```

<211> LENGTH: 76
<212> TYPE: PRT
<213> ORGANISM: Arabidopsis thaliana

<400> SEQUENCE: 24

Met Ala Gln Val Ser Arg Ile Cys Asn Gly Val Gln Asn Pro Ser Leu
1 5 10 15

Ile Ser Asn Leu Ser Lys Ser Ser Gln Arg Lys Ser Pro Leu Ser Val
20 25 30

Ser Leu Lys Thr Gln Gln His Pro Arg Ala Tyr Pro Ile Ser Ser Ser
35 40 45

Trp Gly Leu Lys Lys Ser Gly Met Thr Leu Ile Gly Ser Glu Leu Arg
50 55 60

Pro Leu Lys Val Met Ser Ser Val Ser Thr Ala Cys
65 70 75

<210> SEQ ID NO 25
<211> LENGTH: 72
<212> TYPE: PRT
<213> ORGANISM: Petunia hybrida

<400> SEQUENCE: 25

Met Ala Gln Ile Asn Asn Met Ala Gln Gly Ile Gln Thr Leu Asn Pro
1 5 10 15

Asn Ser Asn Phe His Lys Pro Gln Val Pro Lys Ser Ser Ser Phe Leu
20 25 30

Val Phe Gly Ser Lys Lys Leu Lys Asn Ser Ala Asn Ser Met Leu Val
35 40 45

Leu Lys Lys Asp Ser Ile Phe Met Gln Lys Phe Cys Ser Phe Arg Ile
50 55 60

Ser Ala Ser Val Ala Thr Ala Cys
65 70

<210> SEQ ID NO 26
<211> LENGTH: 69
<212> TYPE: PRT
<213> ORGANISM: Triticum aestivum

<400> SEQUENCE: 26

Met Ala Ala Leu Val Thr Ser Gln Leu Ala Thr Ser Gly Thr Val Leu
1 5 10 15

Ser Val Thr Asp Arg Phe Arg Arg Pro Gly Phe Gln Gly Leu Arg Pro
20 25 30

Arg Asn Pro Ala Asp Ala Ala Leu Gly Met Arg Thr Val Gly Ala Ser
35 40 45

Ala Ala Pro Lys Gln Ser Arg Lys Pro His Arg Phe Asp Arg Arg Cys
50 55 60

Leu Ser Met Val Val
65

<210> SEQ ID NO 27
<211> LENGTH: 171
<212> TYPE: DNA
<213> ORGANISM: Pisum sativum

<400> SEQUENCE: 27 atggcttcta tgatatcctc ttccgctgtg acaacagtca gccgtgcctc tagggggcaa 60 tccgccgcaa tggctccatt cggcggcctc aaatccatga ctggattccc agtgaggaag 120 gtcaacactg acattacttc cattacaagc aatggtggaa gagtaaagtg c 171

<210> SEQ ID NO 28
<211> LENGTH: 255
<212> TYPE: DNA
<213> ORGANISM: Arabidopsis thaliana

<400> SEQUENCE: 28 atggcttcct ctatgctctc ttccgctact atggttgcct ctccggctca ggccactatg 60 gtcgctcctt tcaacggact taagtcctcc gctgccttcc cagccacccg caaggctaac 120 aacgacatta cttccatcac aagcaacggc ggaagagtta actgtatgca ggtgtggcct 180 ccgattgaaa agaagaagtt tgagactctc tcttaccttc ctgaccttac cgattccggt 240 ggtcgcgtca actgc 255

<210> SEQ ID NO 29
<211> LENGTH: 228
<212> TYPE: DNA
<213> ORGANISM: Arabidopsis thaliana

<400> SEQUENCE: 29 atggcgcaag ttagcagaat ctgcaatggt gtgcagaacc catctcttat ctccaatctc 60 tcgaaatcca gtcaacgcaa atctccctta tcggtttctc tgaagacgca gcagcatcca 120 cgagcttatc cgatttcgtc gtcgtgggga ttgaagaaga gtgggatgac gttaattggc 180 tctgagcttc gtcctcttaa ggtcatgtct tctgtttcca cggcgtgc 228

<210> SEQ ID NO 30
<211> LENGTH: 228
<212> TYPE: DNA
<213> ORGANISM: Artificial sequence
<220> FEATURE:
<223> OTHER INFORMATION: Artificial primer

<400> SEQUENCE: 30 atggcgcaag ttagcagaat ctgcaatggt gtgcagaacc catctcttat ctccaatctc 60 tcgaaatcca gtcaacgcaa atctccctta tcggtttctc tgaagacgca gcagcatcca 120 cgagcttatc cgatttcgtc gtcgtgggga ttgaagaaga gtgggatgac gttaattggc 180 tctgagcttc gtcctcttaa ggtcatgtct tctgtttcca cggcgtgc 228

<210> SEQ ID NO 31
<211> LENGTH: 216
<212> TYPE: DNA
<213> ORGANISM: Artificial sequence
<220> FEATURE:
<223> OTHER INFORMATION: Artificial primer

<400> SEQUENCE: 31 atggcccaga tcaacaacat ggcccagggc atccagaccc tgaaccctaa ctctaacttc 60 cacaagccgc aagtgcccaa gtctagctcc ttcctcgtgt tcggctccaa gaagctcaag 120 aatagcgcca attccatgct ggtcctgaag aaagactcga tcttcatgca gaagttctgc 180 tcctttcgca tcagtgcttc ggttgcgact gcctgc 216

<210> SEQ ID NO 32
<211> LENGTH: 207
<212> TYPE: DNA
<213> ORGANISM: Artificial sequence
<220> FEATURE:
<223> OTHER INFORMATION: Artificial primer -continued

```
<400> SEQUENCE: 32

atggcggcac tggtgacctc ccagctcgcg acaagcggca ccgtcctgtc ggtgacggac     60

cgcttccggc gtcccggctt ccagggactg aggccacgga acccagccga tgccgctctc    120

gggatgagga cggtgggcgc gtccgcggct cccaagcaga gcaggaagcc acaccgtttc    180

gaccgccggt gcttgagcat ggtcgtc                                        207
```

What is claimed is:

1. A method for controlling weed growth in a crop-growing environment comprising:

a) applying a herbicidally effective amount of [an auxin-like] *dicamba* herbicide to a crop-growing environment;

b) planting a transgenic seed of a dicotyledonous plant comprising a nucleic acid encoding a polypeptide having dicamba-degrading enzymatic activity in soil of the crop-growing environment within 21 days of applying the herbicide; and c) allowing the seed to germinate into a plant.

2. The method of claim 1, wherein the herbicide is applied prior to, concurrently with, or after the planting of the seed.

3. The method of claim 1, wherein the transgenic seed is planted in the soil within about 12, 10, 7, or 3 days before or after the herbicide is applied.

4. The method of claim 1, wherein the transgenic seed germinates from between about 18 days and 0 days after treating the soil.

5. The method of claim 1, wherein the transgenic seed germinates from between about 14 days and 0 [day] *days* after treating the soil.

6. The method of claim 1, wherein the transgenic seed germinates from between about 7 days and 0 days after treating the soil.

[7. The method of claim 1, wherein the auxin-like herbicide is selected from the group consisting of a phenoxy carboxylic acid compound, a benzoic acid compound, a pyridine carboxylic acid compound, a quinoline carboxylic acid compound, and a benazolinethyl compound.]

[8. The method of claim 7, wherein the phenoxy carboxylic acid compound is selected from the group consisting of: 2,4-dichlorophenoxyacetic acid, (4-chloro-2-methylphenoxy) acetic acid (MCPA), and 4-(2,4-dichlorophenoxy) butyric acid (2,4-DB).]

[9. The method of claim 8, wherein the herbicidally effective amount of 2,4-dichlorophenoxyacetic, (4-chloro-2-methylphenoxy) acetic acid (MCPA), or 4-(2,4-dichlorophenoxy) butyric acid (2,4-DB) is lower than about 1120 g/ha.]

[10. The method of claim 7, wherein the benzoic acid compound is dicamba.]

11. The method of claim [10] *1*, wherein the herbicidally effective amount of dicamba is from about 2.5 g/ha to about 10,080 g/ha.

12. The method of claim 1, wherein the nucleic acid is selected from the group consisting of (1) a nucleic acid sequence encoding the polypeptide of SEQ ID NO: 6, (2) a nucleic acid sequence comprising the sequence of SEQ ID NO: 5, (3) a nucleic acid sequence that hybridizes to a complement of the nucleic acid sequence of SEQ ID NO: 5 under conditions of 5×SSC, 50% formamide and 42° C., (4) a nucleic acid sequence having at least 70% sequence identity to the nucleic acid sequence of SEQ ID NO: 5, and (5) a nucleic acid sequence encoding a polypeptide having at least 70% sequence identity to the polypeptide sequence of SEQ ID NO:6.

13. The method of claim 1, wherein the dicotyledonous plant is selected from the group consisting of alfalfa, beans, broccoli, cabbage, carrot, cauliflower, celery, cotton, cucumber, eggplant, lettuce, melon, pea, pepper, pumpkin, radish, rapeseed, spinach, soybean, squash, tomato, and watermelon.

14. The method of claim 13, wherein the dicotyledonous plant is a soybean, cotton or rapeseed plant.

15. The method of claim 1, further comprising applying a second treatment of [an auxin-like] *dicamba* herbicide after the seed germinates.

16. The method of claim 15, wherein the second treatment is carried out at a time selected from the group consisting of between about the V1 to V2 and V3 to V4 stages, before flowering, at flowering, after flowering, and at seed formation.

17. The method of claim 1, *further* comprising allowing a spray drift from an application of [auxin-like] *dicamba* herbicide to a second crop-growing environment to contact said plant, wherein the plant is tolerant to the spray drift.

18. A method for controlling a glyphosate tolerant weed in a field comprising:

a) planting a transgenic seed in a field comprising a glyphosate tolerant weed or a seed thereof, wherein the seed comprises a transgene conferring glyphosate tolerance and a transgene encoding dicamba monooxygenase, the transgene encoding dicamba monooxygenase which displays dicamba-degrading enzymatic activity comprising a nucleic acid sequence selected from the group consisting of (1) a nucleic acid sequence encoding the polypeptide of SEQ ID NO:6, (2) a nucleic acid sequence comprising the sequence of SEQ ID NO:5, and (3) a nucleic acid sequence encoding a polypeptide with at least 90% sequence identity to the polypeptide of SEQ ID NO:6, wherein the polypeptide has dicamba monooxygenase activity;

b) growing the seed into a plant; and c) treating the field with an amount of [an auxin-like] *dicamba* herbicide and glyphosate effective to control weed growth of the glyphosate tolerant weed.

19. The method of claim 18, wherein the transgene conferring glyphosate tolerance encodes a protein selected from the group consisting of glyphosate resistant 5-enolpyruvylshikimate-3-phosphate synthase (EPSPS), glyphosate oxidoreductase (GOX), glyphosate-N-acetyl transferase (GAT) and glyphosate decarboxylase.

20. The method of claim 19, wherein the transgene encoding GAT comprises the nucleic acid sequence of SEQ ID NO:18, or encodes the polypeptide of SEQ ID NO:19.

21. The method of claim 18, wherein the seed is from a dicotyledonous plant selected from the group consisting of alfalfa, beans, broccoli, cabbage, carrot, cauliflower, celery, cotton, cucumber, eggplant, lettuce, melon, pea, pepper, pumpkin, radish, rapeseed, spinach, soybean, squash, tomato, and watermelon.

22. The method of claim 21, wherein the dicotyledonous plant is a soybean, cotton or rapeseed plant.

23. The method of claim 18, wherein treating the field is carried out at a time selected from the group consisting of between about the V1 to V2 and V3 to V4 leaf stages, before flowering, at flowering, after flowering, and at seed formation.

24. The method of claim 18, wherein treating the field is carried out after the seed germinates.

25. The method of claim 18, wherein treating the field is carried out about four weeks, three weeks, two weeks, 1 week, or 0 weeks before step a).

26. The method of claim 18, wherein treating the field is carried out concurrently with the planting of the seed.

27. The method of claim 18, wherein the transgenic seed is planted in the soil within about 15, 12, 10, 7 or about 3 days before or after applying the herbicide.

28. The method of claim 18, wherein the transgenic seed germinates from between about 0 and about 18, 14, 7, or 1 days after treating the soil.

[29. The method of claim 18, wherein the auxin-like herbicide is selected from the group consisting of a phenoxy carboxylic acid compound, benzoic acid compound, pyridine carboxylic acid compound, quinoline carboxylic acid compound, and benazolinethyl compound.]

[30. The method of claim 29, wherein the phenoxy carboxylic acid compound is selected from the group consisting of 2,4-dichlorophenoxyacetic acid and (4-chloro-2-methylphenoxy) acetic acid.]

[31. The method of claim 30, wherein the amount of 2,4-dichlorophenoxyacetic compound is lower than about 1120 g/ha.]

[32. The method of claim 30, wherein the amount of 2,4-dichlorophenoxyacetic compound is lower than about 280 g/ha.]

[33. The method of claim 30, wherein the amount of (4-chloro-2-methylphenoxy) acetic acid compound is lower than about 1120 g/ha.]

[34. The method of claim 30, wherein the amount of (4-chloro-2-methylphenoxy) acetic acid compound is lower than about 280 g/ha.]

[35. The method of claim 29, wherein the benzoic acid is dicamba.]

36. The method of claim [35] *18*, wherein the amount of dicamba is from about 2.5 g/ha to about 10,080 g/ha.

37. The method of claim 23, wherein the amount of glyphosate is from about 200 g/ha to about 1,600 g/ha.

38. The method of claim 18, wherein [the auxin-like] *dicamba* herbicide and glyphosate are applied substantially simultaneously.

[39. A method for controlling weed growth in a field comprising:

a) applying a herbicidally effective amount of an auxin-like herbicide other than dicamba to a field, wherein the field comprises a transgenic dicotyledonous plant comprising a nucleic acid encoding a polypeptide having dicamba degrading enzymatic activity or is planted with a seed that germinates into said transgenic dicotyledonous plant within 21 days of applying the herbicide, wherein the herbicidally effective amount is an amount that does not damage the transgenic dicotyledonous plant but will damage a plant of the same genotype that lacks the nucleic acid encoding a polypeptide having dicamba degrading enzymatic activity, wherein the nucleic acid is selected from the group consisting of (1) a nucleic acid sequence encoding the polypeptide of SEQ ID NO:6, (2) a nucleic acid sequence comprising the sequence of SEQ ID NO:5, (3) a nucleic acid sequence encoding a polypeptide with at least 90% sequence identity to the polypeptide of SEQ ID NO:6, wherein the polypeptide has dicamba monooxygenase activity; and b) allowing the transgenic dicotyledonous plant to grow.]

[40. The method of claim 39, wherein step a) comprises applying the herbicidally effective amount of an auxin-like herbicide to a growing environment adjacent to a growing environment comprising the transgenic dicotyledonous plant and allowing the herbicide to drift onto the plant or soil in which the plant grows.]

[41. The method of claim 39, wherein the auxin-like herbicide is selected from the group consisting of a phenoxy carboxylic acid compound, benzoic acid compound, pyridine carboxylic acid compound, quinoline carboxylic acid compound, and benazolinethyl compound.]

[42. The method of claim 41, wherein the phenoxy carboxylic acid compound is selected from the group consisting of 2,4-dichlorophenoxyacetic acid, (4-chloro-2-methylphenoxy) acetic acid and 4-(2,4-dichlorophenoxy) butyric acid (2,4-DB).]

[43. The method of claim 39, wherein step b) comprises allowing the transgenic dicotyledonous plant to grow to maturity.]

[44. The method of claim 39, wherein the transgenic dicotyledonous plant is a selected from the group consisting of alfalfa, beans, broccoli, cabbage, carrot, cauliflower, celery, cotton, cucumber, eggplant, lettuce, melon, pea, pepper, pumpkin, radish, rapeseed, spinach, soybean, squash, tomato, and watermelon.]

[45. The method of claim 39, wherein the transgenic dicotyledonous plant is a soybean, cotton or rapeseed plant.]

46. A method for increasing the efficiency of use of a herbicide delivery device comprising:

a) obtaining a device that has been used to deliver a first composition comprising [an auxin-like] *dicamba* herbicide;

b) delivering a second composition to the field using the device without first completely washing the device so that a herbicide residue comprising [the auxin-like] *dicamba* herbicide remains in the device and is delivered with the second composition to the field, wherein the field comprises a transgenic dicotyledonous plant expressing a nucleic acid encoding dicamba monooxygenase which displays dicamba-degrading enzymatic activity or is planted with a seed that germinates into said transgenic dicotyledonous plant, and wherein the herbicide residue is present in an amount that does not damage the transgenic dicotyledonous plant but will damage a plant of the same genotype that lacks the nucleic acid encoding dicamba monooxygenase which displays dicamba-degrading enzymatic activity.

47. The method of claim 46, wherein the nucleic acid is selected from the group consisting of (1) a nucleic acid sequence encoding the polypeptide of SEQ ID NO:6, (2) a nucleic acid sequence comprising the sequence of SEQ ID NO:5, (3) a nucleic acid sequence that hybridizes to a complement of the nucleic acid sequence of SEQ ID NO:5 under conditions of 5× SSC, 50% formamide and 42° C., (4) a nucleic acid sequence having at least 70% sequence identity to the nucleic acid sequence of SEQ ID NO:5, and (5) a nucleic acid sequence encoding a polypeptide having at least 70% sequence identity to the polypeptide sequence of SEQ ID NO:6.

[48. The method of claim 46, wherein the auxin-like herbicide is selected from the group consisting of a phenoxy carboxylic acid compound, benzoic acid compound, pyridine carboxylic acid compound, quinoline carboxylic acid compound, and benazolinethyl compound.]

[49. The method of claim 48, wherein the phenoxy carboxylic acid compound is 2,4-dichlorophenoxyacetic acid, (4-chloro-2-methylphenoxy) acetic acid (MCPA), or 4-(2,4-dichlorophenoxy) butyric acid (2,4-DB).]

[50. The method of claim 48, wherein the benzoic acid compound is dicamba.]

51. The method of claim [48] *46*, wherein the dicotyledonous plant is selected from the group consisting of alfalfa, beans, broccoli, cabbage, carrot, cauliflower, celery, cotton, cucumber, eggplant, lettuce, melon, pea, pepper, pumpkin, radish, rapeseed, spinach, soybean, squash, tomato, and watermelon.

52. The method of claim 51, wherein the dicotyledonous plant is a soybean, cotton or rapeseed plant.

53. A method for controlling weed growth in a crop-growing environment comprising:

a) planting a transgenic seed in a field comprising a weed or a seed thereof, wherein the transgenic seed comprises a transgene conferring glyphosate tolerance and a transgene conferring dicamba tolerance;

b) treating the field with a herbicidally effective amount of dicamba, glyphosate, or a mixture thereof, wherein the planting and the treating is done in a single pass through the field; and c) growing the transgenic seed into a plant.

54. The method of claim 53, wherein the transgene conferring glyphosate tolerance encodes a protein selected from the group consisting of glyphosate resistant 5-enolpyruvylshikimate-3-phosphate synthase, glyphosate oxidoreductase, and glyphosate-N-acetyl transferase, and glyphosate decarboxylase.

55. The method of claim 54, wherein the transgene encoding GAT comprises the nucleic acid sequence of SEQ ID NO:18, or encodes the polypeptide of SEQ ID NO:19.

56. The method of claim 53, wherein the transgene conferring dicamba tolerance encodes a dicamba monooxygenase comprising a nucleic acid sequence selected from the group consisting of (a) a nucleic acid sequence encoding the polypeptide of SEQ ID NO:6, (b) a nucleic acid sequence comprising the sequence of SEQ ID NO:5, (c) a nucleic acid sequence that hybridizes to a complement of the nucleic acid sequence of SEQ ID NO:5 under conditions of 5× SSC, 50% formamide and 42° C., (d) a nucleic acid sequence having at least 70% sequence identity to the nucleic acid sequence of SEQ ID NO:5, and e) a nucleic acid sequence encoding a polypeptide having at least 70% sequence identity to the polypeptide sequence of SEQ ID NO:6.

57. The method of claim 53, wherein the transgenic seed if from a dicotyledonous plant is selected from the group consisting of alfalfa, beans, broccoli, cabbage, carrot, cauliflower, celery, cotton, cucumber, eggplant, lettuce, melon, pea, pepper, pumpkin, radish, rapeseed, spinach, soybean, squash, tomato, and watermelon seed.

58. The method of claim 57, wherein the dicotyledonous plant is a soybean, cotton or rapeseed plant.

59. The method of claim 53, wherein the amount of dicamba is from about 2.5 g/ha to about 10,080 g/ha.

60. The method of claim 53, wherein the amount of glyphosate is from about 200 g/ha to about 1,600 g/ha.

* * * * *

UNITED STATES PATENT AND TRADEMARK OFFICE

CERTIFICATE OF CORRECTION

PATENT NO. : RE45,048 E
APPLICATION NO. : 13/751021
DATED : July 22, 2014
INVENTOR(S) : Paul C. C. Feng It is certified that error appears in the above-identified patent and that said Letters Patent is hereby corrected as shown below:

In The Claims

Column 75, Line 65, please delete "C.," and insert --C[.],--

Column 78, Line 62, please delete "C.," and insert --C[.],--

Column 80, Line 15, please delete "C.," and insert --C[.],--

Signed and Sealed this
Fourteenth Day of April, 2015

Michelle K. Lee

Michelle K. Lee
*Director of the United States Patent and Trademark Office*